United States Patent
Sasaki et al.

(10) Patent No.: US 7,220,227 B2
(45) Date of Patent: May 22, 2007

(54) ADAPTER FOR ENDOSCOPE AND ENDOSCOPE

(75) Inventors: Isao Sasaki, Tokyo (JP); Tsuyoshi Nakagawa, Tokyo (JP); Yasushi Ohkoshi, Tokyo (JP); Jin Ito, Tokyo (JP); Kenichi Adachi, Northport, NY (US); Hiroaki Kubokawa, Sagamihara (JP); Hidenobu Kimura, Tokyo (JP); Osamu Tamada, Tokyo (JP); Tae Mitsuya, Sagamihara (JP); Takashi Otawara, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/899,693

(22) Filed: Jul. 27, 2004

(65) Prior Publication Data

US 2005/0065399 A1    Mar. 24, 2005

(30) Foreign Application Priority Data

Jul. 29, 2003 (JP) ............................ P2003-281858
May 13, 2004 (JP) ............................ P2004-143617

(51) Int. Cl.
*A61B 1/00* (2006.01)
(52) U.S. Cl. ...................... 600/154; 600/102; 600/106; 600/153
(58) Field of Classification Search ............... 600/102, 600/104, 106
See application file for complete search history.

(56) References Cited

U.S. PATENT DOCUMENTS 5,209,219 A * 5/1993 Hollobaugh ................. 600/154
6,299,576 B1 * 10/2001 Ouchi ......................... 600/106
6,315,774 B1 * 11/2001 Daniel et al. ................. 606/15
6,352,503 B1 * 3/2002 Matsui et al. ............... 600/104
6,827,683 B2 * 12/2004 Otawara ..................... 600/123
2002/0087100 A1   7/2002 Onuki et al.
2002/0091303 A1   7/2002 Ootawara et al.
2004/0015050 A1 * 1/2004 Goto et al. ................. 600/104

FOREIGN PATENT DOCUMENTS

| DE | 41 15 007 A1 | 11/1992 |
| JP | 8-187292 | 7/1996 |
| JP | 2002-34905 | 2/2002 |
| WO | WO 00/69500 | 11/2000 |

* cited by examiner

*Primary Examiner*—Linda C. M. Dvorak
*Assistant Examiner*—Matthew J. Kasztejna
(74) *Attorney, Agent, or Firm*—Scully, Scott, Murphy & Presser PC

(57) ABSTRACT

An adapter for an endoscope of the present invention includes: a locking device for attaching and detaching that attaches and locks this adapter for an endoscope onto a predefined position on an endoscope control part; and a first treatment tool locking device that keeps a treatment tool at a first predefined position. Furthermore, at the first predefined position, a guidewire entry aperture of the treatment tool and an entry aperture of a forceps plug are separated in such a way as to face each other along substantially the same line.

12 Claims, 27 Drawing Sheets

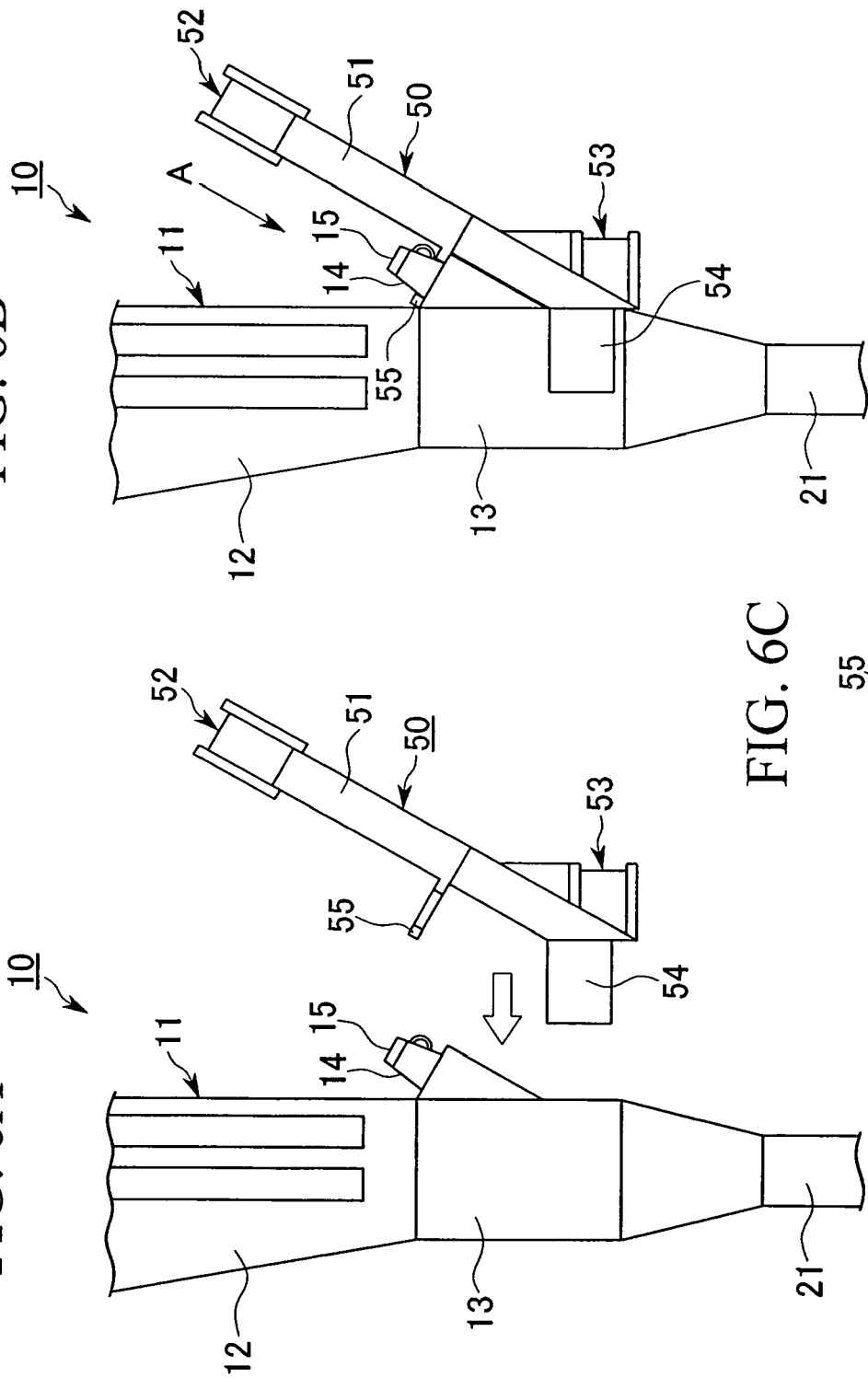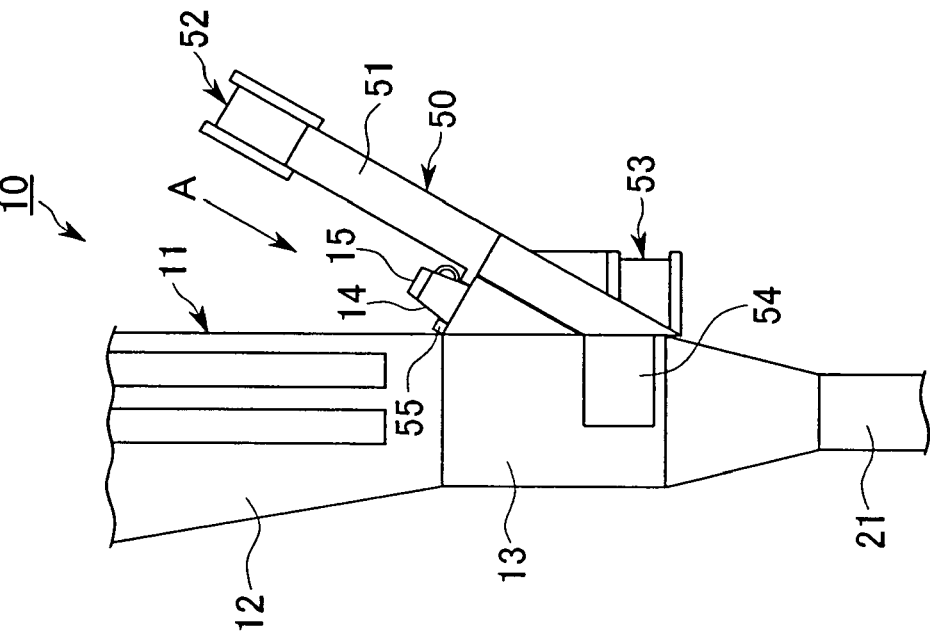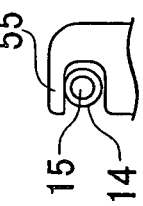

ADAPTER FOR ENDOSCOPE AND ENDOSCOPE

BACKGROUND OF THE INVENTION

Priority is claimed on Japanese Patent Application No. 2003-281858, filed Jul. 29, 2003 and Japanese Patent Application No. 2004-143617, filed May 13, 2004, the contents of which are incorporated herein by reference.

FIELD OF THE INVENTION

The present invention relates to an adapter for an endoscope and to an endoscope applied as the endoscope in an operation that requires the changing of treatment tools such as a catheter and so on using a guide wire as in the case of, for example, endoscopy and endoscopic surgery of the pancreas and bile duct system.

DESCRIPTION OF THE RELATED ART

Recently, endoscopic treatment has been increasingly employed in the treatment of disorders in the alimentary canal system and pancreas and bile duct system. In current treatments using an endoscope for the pancreas and bile duct system, as well as diagnostic treatment in which a contrast image of the bile duct and the pancreatic duct is captured endoscopically, there are also therapeutic treatments and so on in which a gallstone in the choledoch duct, for example, is retrieved using a balloon or gripping treatment tool.

Also, in the case of endoscopic treatment of the pancreatic duct, bile duct or hepatic duct, usually, the end part of the endoscope insertion part is inserted close to the duodenal papilla, and then a treatment tool such as a catheter is selectively inserted into the pancreatic duct or bile duct using a guide wire as a guide under X-ray fluoroscopy. Also, the shaft of the treatment tool (insertion part) is inserted through a forceps channel provided at the insertion part of the endoscope, and meanwhile, the guide wire is inserted passing completely through the guide wire lumen provided in the shaft.

Since various kinds of treatment tools are sequentially changed and used in such endoscopic treatments, quick and reliable changing of the treatment tool is necessary in order to shorten the treatment time and reduce strain on the patient.

Here, to briefly describe the conventional operation of changing the treatment tool, after the end part of the guide wire is inserted to the required position, this is used as a guide and the end of the shaft of the treatment tool to be used first is inserted to the target position. After this, when the treatment tool is to be changed, the used treatment tool needs to be pulled out leaving only the guide wire. Consequently, at least one person other than the operator is required to be an assistant to the operator, and a cooperative operation in which the operator pulls out the shaft of the treatment tool and at the same time the assistant feeds the guide wire in equal amounts in the insertion direction opposite to the shaft, needs to be carried out. Specifically, by the shaft and the guide wire relatively moving in equal amounts in opposing directions, it becomes substantially possible to pull out only the treatment tool, leaving the guide wire.

A cooperative operation like this requires high proficiency because the timing and amounts of pulling out and feeding in need to match substantially. Accordingly, in order to facilitate the treatment tool changing operation mentioned above, it has been proposed to provide a guide wire locking device near the exit aperture of the channel provided at the end of the insertion part of the endoscope. With this conventional technique, even when it is operated by only a single operator, after locking only the guide wire near the exit aperture of the end part of the insertion part, the treatment tool only can be quickly and easily pulled out completely, leaving the guide wire (for example, see Japanese Unexamined Patent Application, First Publication No. 2002-34905).

SUMMARY OF THE INVENTION

An endoscope adapter of the present invention is a freely detachable adapter for an endoscope to be used with an endoscope that is provided with an endoscope control part, which an operator holds in hand and which carries out various operations, and an endoscope insertion part, one end of which is connected to the endoscope control part, and which is inserted into a body cavity from the other end side; and that is constructed so that as a shaft of a treatment tool provided with a guide wire lumen is inserted from a forceps plug provided in the endoscope control part into a forceps channel of the endoscope insertion part, the shaft is to be guided by a guidewire passing through the guide wire lumen, and inserted to a desired position inside the body cavity; the adapter including: a locking device for attaching and detaching that attaches and locks the adapter for an endoscope onto a predefined position on the endoscope control part; and a first treatment tool locking device that keeps the treatment tool at a first predefined position; and at the first predefined position, a guidewire entry aperture of the treatment tool and an entry aperture of the forceps plug are separated in such a way as to face each other along substantially the same line.

The adaptor for an endoscope may further include a second treatment tool locking device which holds the treatment tool at a second predetermined position wherein the guide wire entry aperture at the second predetermined position is made to be in substantially the same direction as the direction of operation of the guide wire in which the end part of the guide wire is moved to a required position in a body cavity.

The locking device for attaching and detaching may have a position determination device.

The first and second treatment tool locking devices may be respectively parts to be locked onto having a substantially circular cross section, and the treatment tool may be locked by engaging a substantially semi-cylindrical, U-shaped part, formed with elastic material and provided on the treatment tool control part, to the periphery of the part to be locked onto.

The adaptor for an endoscope may further include a rod-shaped connection part, wherein the first and second treatment tool locking devices are respectively provided at both ends of the rod-shaped connection part.

The adaptor for an endoscope may further include: a first rod-shaped member, which has the part to be locked onto having a substantially circular cross section provided on its top end side; and a second rod-shaped member, which has the locking device for attaching and detaching provided on its bottom end side, are pivotably connected to the first rod-shaped member, wherein the part to be locked onto with the first and second rod-shaped members held in a straight line is taken to be the first predetermined position, and the part to be locked onto with the first and second rod-shaped members held in a bent shape is taken to be the second predetermined position, and the part to be locked onto is made to be selectively switchable between the first predetermined position and the second predetermined position.

The treatment tool may have a shaft extension part connected to the guidewire entry aperture, and the treatment tool locking device may be provided at the back end of the shaft extension part.

An endoscope according to the present invention is provided with: an endoscope control part, which an operator holds in hand and which carries out various operations; an endoscope insertion part, one end of which is connected to the control part, and which is inserted into a body cavity from the other end side; a forceps plug provided in the endoscope control part; and a first treatment tool locking device that keeps a treatment tool at a first predefined position, wherein the endoscope is constructed so that as a shaft of the treatment tool provided with a guide wire lumen is inserted from the forceps plug into a forceps channel of the endoscope insertion part, the shaft is to be guided by a guidewire passing through the guide wire lumen, and inserted to a desired position inside the body cavity, and wherein at the first predefined position, a guidewire entry aperture of the treatment tool and an entry aperture of the forceps plug are separated in such a way as to face each other along substantially the same line.

The endoscope may further include a second treatment tool locking device which holds the treatment tool at a second predetermined position is provided, wherein the guide wire entry aperture at the second predetermined position is made to be in substantially the same direction as the direction of operation of the guide wire in which the end part of the guide wire is moved to a required position in a body cavity.

The first and second treatment tool locking devices may be respectively parts to be locked onto having a substantially circular cross section, and the treatment tool may be locked by engaging a substantially semi-cylindrical U-shaped part, formed with elastic material and provided on a treatment tool control part to the periphery of the part to be locked onto.

The endoscope may further include a first rod-shaped member, which has a part to be locked onto having a substantially circular cross section, provided on its top end side, and a second rod-shaped member, which is locked on the endoscope control part, are pivotably connected each other, wherein the part to be locked onto with the first and second rod-shaped members held in a straight line is taken to be the first predetermined position, and the part to be locked onto with the first and second rod-shaped members held in a bent shape is taken to be the second predetermined position, and they are made selectively switchable.

The treatment tool may have a shaft extension part connected to the guidewire entry aperture, and the treatment tool locking device may be provided at the back end of the shaft extension part.

BRIEF DESCRIPTION OF THE DRAWINGS

FIGS. 6A to 6C are explanatory diagrams relating to an attachment operation of the endoscope adapter shown in FIG. 2, FIG. 6A showing the status before attachment, FIG. 6B showing the status after locking completion, and FIG. 6C being an auxiliary view of FIG. 6B.

DETAILED DESCRIPTION OF THE INVENTION

Hereinafter, preferred embodiments relating to an endoscope adapter and an endoscope of the present invention are described, with reference to drawings.

Figure 1:
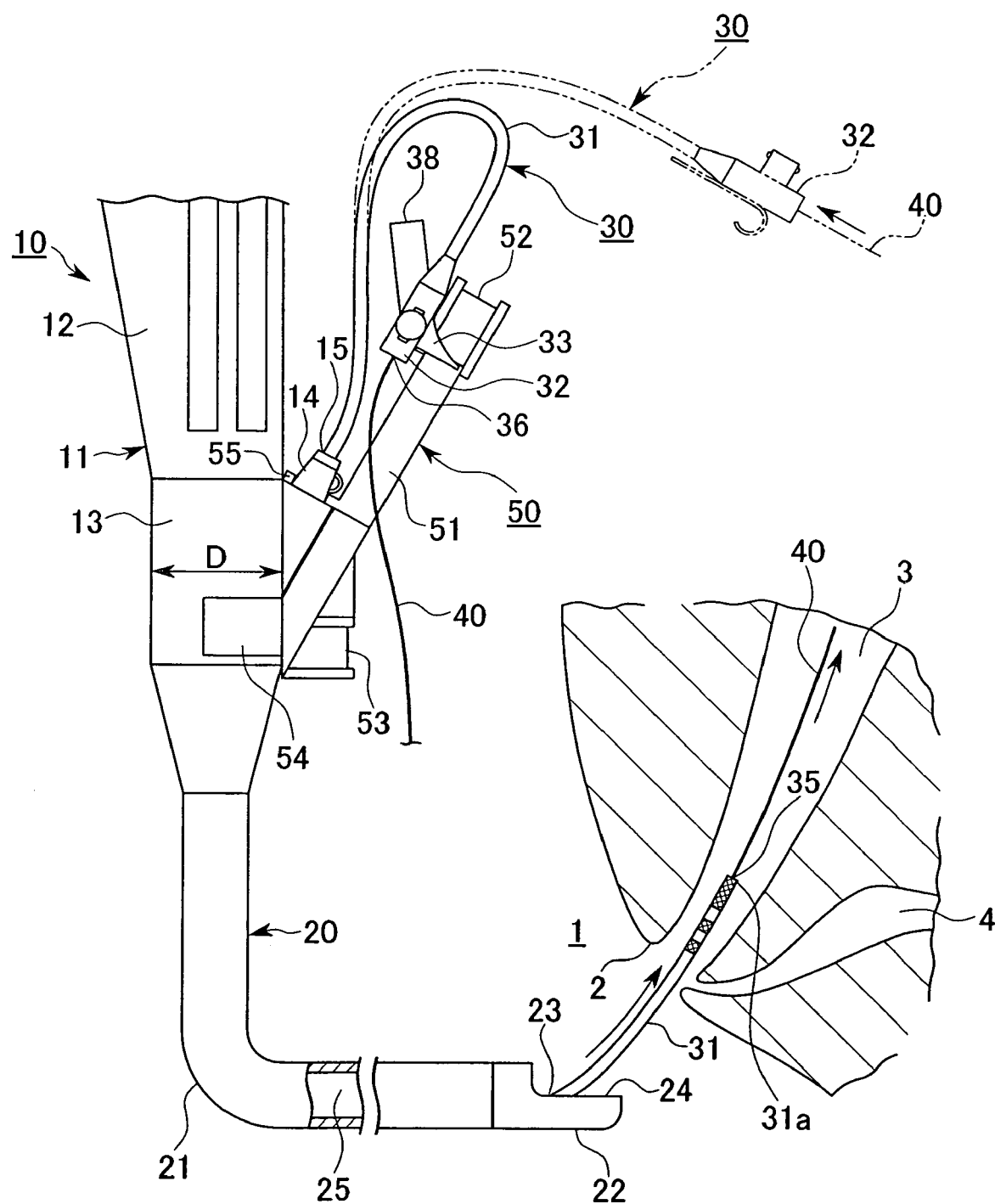
FIG. 1 is a diagram showing an aspect of an endoscope adapter being used in combination with an endoscope and a catheter, as a first embodiment of an endoscope adapter according to the present invention.

In FIG. 1, which shows a first embodiment, a catheter 30, which is a treatment tool used with an endoscope 10, is shown with solid lines in the status of being locked on an endoscope adapter 50 (hereinafter referred to as "adapter"). Also, reference symbol 1 in FIG. 1 denotes a duodenum, reference symbol 2 denotes a duodenal papilla, reference symbol 3 denotes a bile duct, and reference symbol 4 denotes a pancreatic duct.

The endoscope 10 has, as major constituent elements, an endoscope control part 11, which the operator holds in his or her hand to carry out various kinds of operations, and an endoscope insertion part 20, which is inserted into a body cavity such as the duodenum 1 for example. Specifically, the construction of the endoscope 10 is such that the endoscope control part 11 is provided connected to the end of a long and thin hollowed endoscope insertion part 20 on the side close to the hand.

Also, according to its application, the endoscope 10 is appropriately combined with various kinds of external devices not shown, such as a lighting device, an image processing device, a monitor, an input keyboard, a suction pump device and a water supply bottle, in order to establish an endoscope system. The various kinds of external devices mentioned above are usually installed on a shelf that has carriers. Furthermore, among these external devices, the lighting device and the image-processing device are connected to a control part 11 of the endoscope 10 via a universal cord (not shown in the diagram).

Operation levers and operation buttons (not shown in the diagram) for various kinds of treatment operations are provided on a control part base 12 of the endoscope control part 11. Also, a cylindrical part 13 and a forceps valve 14 that bifurcates from the cylindrical part 13 are provided on the bottom end part side of the control part base 12 connected to the endoscope insertion part 20.

An end part 22 is provided on the body cavity insertion side of the endoscope insertion part 20, on the end part of a long thin flexible tube part 21, which is flexible, via a curved part not shown in the diagram. A channel exit aperture 23 is provided on the end part 22, which is positioned at the very end of the flexible tube part 21. One side of the peripheral face of the end part 22 is cut away to form a concave cutaway part 24 thereon, and the channel exit aperture 23 is arranged on one side face of this cutaway part 24. An objective lens for observational optics and a lighting lens for lighting optics not shown in the diagram are arranged in a line on the side of the channel exit aperture 23. Also, an air/water feeding nozzle not shown in the diagram is provided in a protruding state on the back end wall face of the cut away part 24 in order to carry out cleaning of the objective lens and the lighting lens.

A forceps valve 14 provided so as to bifurcate from the cylindrical part 13 has an entry aperture 15 into which various kinds of treatment tool such as a shaft 31 of the catheter 30 described later are inserted, and this entry aperture 15 leads to the forceps channel 25 which is a passageway for the treatment tool to pass through the endoscope insertion part 20. This forceps channel 25 passes through the endoscope insertion part 20 in the longitudinal direction (axial direction) and links to the channel exit aperture 23 of the end part 22. Also, as specific examples of the operation levers and the operation buttons mentioned above, there are an bending operation part which moves the bending part of the endoscope insertion part 20 up and down and left and right, an air/water feeding button which selectively squirts gas and liquid into the air/water feeding nozzle of the end part 22, and a suction operation button which selectively creates suction at the channel exit aperture 23 of the end part through the forceps channel 25 and retrieves mucous and so forth within the body cavity.

As shown in FIGS. 3 to 5C, the catheter 30 is constructed having; a long thin shaft 31 that is passed through the forceps channel 25 of the endoscope 10, a substantially cylindrical treatment tool control part 32 provided on one end side of the shaft 31, and a treatment tool locking part 33 to lock the treatment tool control part 32 at a predetermined position.

The shaft 31 has a guidewire lumen 34 passing through in the longitudinal direction (axial direction), which is the passageway through which the guidewire 40 is passed, and an on an end part 31a, on the side which is inserted into body cavity, a guidewire lumen exit aperture 35 is provided. Also, the guidewire lumen 34 has sufficient clearance such that relative movement in the space between it and the outer periphery of the guidewire 40 will not be disturbed, since a space part of doughnut-shaped cross section formed between the inner peripheral face of the guidewire lumen 34 and the guidewire 40 is used as a flow channel for contrast medium and so forth.

The treatment tool control part 32 is provided on the end part of the shaft 31 on the side close to the hand (forceps valve 14 side), and it has a guidewire lumen entry aperture 36, a fluid feeding cap 37, which connects to the guidewire lumen 34 and which is the entry through which contrast medium is supplied, and a U-shaped part 33, which is the treatment tool locking part for locking the treatment tool control part 32 at the predetermined position.

Figure 5A:
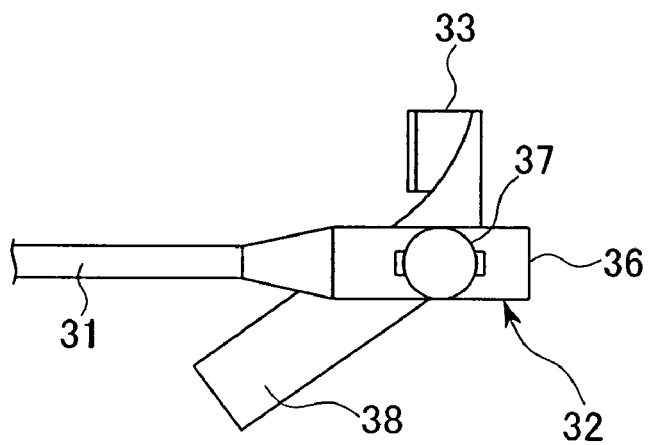
FIGS. 5A to 5C are schematic diagrams showing the periphery of the treatment tool control part shown in FIG. 4, FIG. 5A being a plan view thereof, FIG. 5B being a front view thereof, and FIG. 5C being a right side view thereof.
Figure 5B:
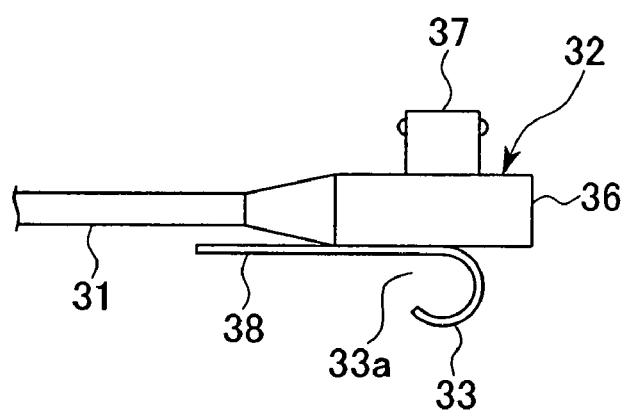
Figure 5C:
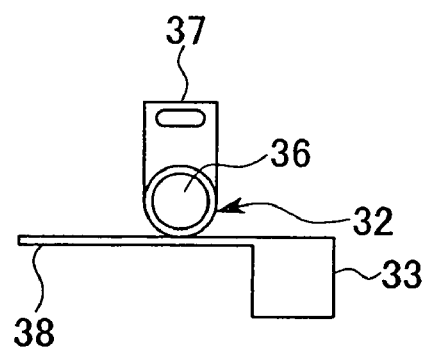

As shown in FIG. 5B, the U-shaped part 33 is a cylindrical member that is made of a plate of elastic material formed in a shape of substantially semi-circular cross section. Because one end part side of this U-shaped part 33 is locked to and supported by the treatment tool control part 32 and the U-shaped part 33 is engaged to the part to be locked onto of the adapter 50, which is described later, to lock it, the U-shaped part 33 has a segmental aperture 33a for passing through. Also, the inner diameter of the U-shaped part 33 is configured to be equal or slightly less than the external diameter D of the cylindrical part 13 in order to make it possible also to directly lock the treatment tool control part 32 to the endoscope control part 11. That is, it is made to be fitted and locked to the peripheral face of the cylindrical part 13 by virtue of the elasticity of the U-shaped part 33.

Furthermore, in order to make the operation of removing the U-shaped part 33 from the part to be locked onto easy, that is, in order that a force acts in the direction in which the segmental arch aperture 33a of the U-shaped part 33 is widened by elastically deforming it by the principle of leverage, a protruding knob 38 is provided.

Figure 2:
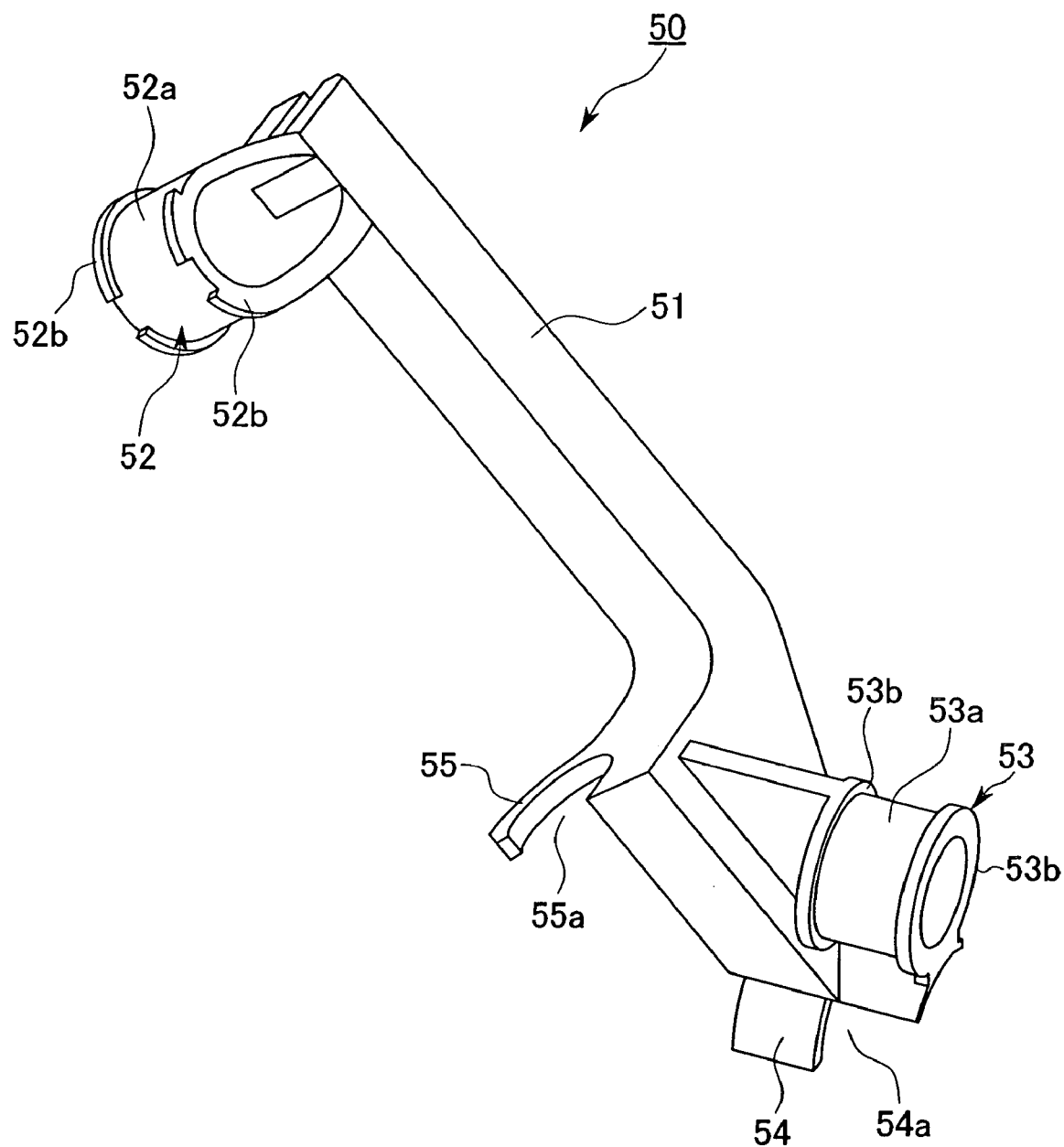
FIG. 2 is a perspective view showing a configuration example of the endoscope adapter shown in FIG. 1.
Figure 3:
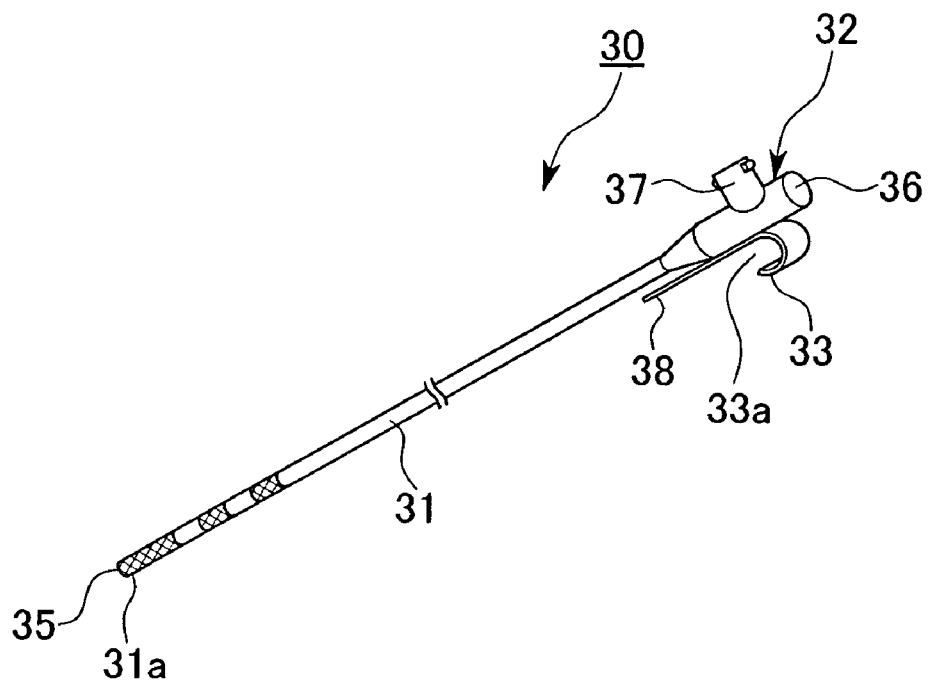
FIG. 3 is a perspective view showing a configuration example of a catheter.
Figure 4:
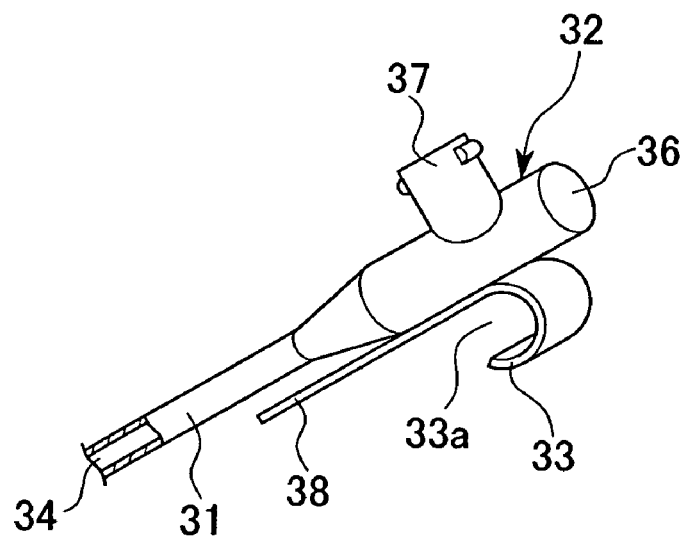
FIG. 4 is a perspective view showing an enlargement of the periphery of a treatment tool control part in connection with the catheter shown in FIG. 3.

As shown in FIG. 2, the adapter 50 is attached to the cylindrical part 13 of the endoscope 10 in such a way as to be freely detachable, and is a separate member that changes the direction of the treatment tool control part 32 of the catheter 30 substantially 180 degrees and locks it. Specifically, the treatment tool control part 32 of the catheter 30 is locked in the position where the entry aperture 15 of the forceps valve 14 and the guidewire lumen entry aperture 36 of the treatment tool control part 32 are separated and opposing each other on substantially the same straight line.

Here, a construction example of the adapter 50 is described, with reference to FIG. 2.

The construction of the adapter 50 is such that two parts to be locked onto having substantially circular cross sections are provided at both ends of a connection part 51 having, for example, a rod shape. One part to be locked onto is a first catheter locking part 52 on the top end part side, and is a first treatment tool locking device provided to hold the treatment tool control part 32 of the catheter 30 mentioned above to the first predetermined position, that is, the locking position where the operation of changing the catheter 30 is carried out.

Also, the other part to be locked onto is a second catheter locking part 53 on the bottom end part side, and is a second treatment tool locking device provided to hold the treatment tool control part 32 of the catheter 30 mentioned above to the second predetermined position, the locking position where normal operations, such as inserting the end of the guidewire 40 that runs through the guidewire lumen of the catheter 30 to the desired position and so on, are carried out.

An endoscope locking part 54 is provided on the bottom part side of the connection part 51 as a device for attaching and detaching to attach and lock the adapter 50 in a predetermined position on the endoscope control part 11. For this endoscope locking part 54, for example, an elastic plate member formed to be substantially semi-cylindrical and locked on the connection part 51 is employed and the segmental arch part becomes an entry part 54a through which the cylindrical part 13 passes when attaching. In this case the inner diameter of the substantially semi-circular cylinder of the endoscope locking part 54 is set to a value equal to, or slightly less than the outer diameter D of the cylindrical part 13 so that it locks onto the cylindrical part 13 of the control part body 11. That is, by virtue of the elasticity on the endoscope locking part 54 side, it fits and locks to the side of the cylindrical part 13.

Furthermore, as long as the adapter 50 can be freely attached and detached at the predetermined position of the endoscope control part 11 having the parts to be locked onto in the first and second predetermined positions, the locking device for attaching and detaching is not limited to the endoscope locking part 54 mentioned above.

Incidentally, the first catheter locking part 52 mentioned above is constructed having a first cylindrical part 52a that has an external diameter configured to be equal to the external diameter D of the cylindrical part 13, and a pair of flange parts 52b and 52b provided on the ends of both sides of the first cylindrical part 52a. Correspondingly, the second catheter locking part 53 is constructed having a second cylindrical part 53a that has an external diameter configured to be equal to the external diameter D of the cylindrical part 13, and a pair of flange parts 53b and 53b provided on the ends of both sides of the second cylindrical part 53a.

Here, the external diameters of the first cylindrical part 52a and the second cylindrical part 53a are configured to be equal to the external diameter D of the cylindrical part 13 of the control part body 11 in order to engage and hold the U-shaped part 33 provided on the treatment tool control part 32 of the catheter 30 mentioned above. Also, the flange parts 52b and 53b provided on both ends of the first and second cylindrical parts 52a and 53a are to prevent the engaged U-shaped part 33 from moving in an axial direction and disengaging.

Incidentally, in the present invention, in order to make it possible for the U-shaped part 33 to be attached and detached to and from the cylindrical part 13, the inner diameter of the U-shaped part 33 and the external diameters of the first cylindrical part 52a and the second cylindrical part 53a are made to match to the external diameter D of the cylindrical part 13. However, if directly attaching and detaching the U-shaped part 33 to and from the cylindrical part 13 is not a consideration, only the inner diameter of the U-shaped part 33 and the external diameters of the first cylindrical part 52a and the second cylindrical part 53a need to match, or substantially match within the range of elastic deformation of the U-shaped part 33.

Furthermore, the first catheter locking part 52 and the second catheter locking part 53 provided on the connection part 51 are made to respectively face in different directions to the straight-line connection part 51. One of them, the first catheter locking part 52, can lock the guidewire lumen entry aperture 36 of the treatment tool control part 32 making it opposed to the entry aperture of the forceps valve 14 on substantially the same straight line, while the adapter 50 is locked in the predetermined position, and the other one of them, the second catheter locking part 53, can lock the guidewire entry aperture direction of the treatment tool control part 32 so that it intersects with the entry aperture direction of the forceps valve 14.

Furthermore, a contact part 55 constructed of a plate member having a substantially U shape cutaway part 55a as a position determination device is provided on the adapter 50 mentioned above. This contact part 55 is provided and fixed on the connection part 51, and the forceps valve 14 extending out of the control part body 11 is engaged as it enters into the cutaway part 55a, so that the contact part 55 has a function that contributes to position determination and definite locking of the adapter 50. That is, the forceps valve 14 interferes and blocks the contact part 55 in any position except for the predetermined locking position, so that it becomes difficult to fit, engage and lock the adapter 50 on the cylindrical part 13, and when the adapter 50 is positioned at the predetermined locking position, the cutaway part 55a of the contact part 55 latches onto the forceps plug 14 and prevents dislodgement due to unexpected external force.

Next, the effect of the adapter 50 of the construction mentioned above is described in connection with the operation of changing treatment tools with the endoscope 10.

FIGS. 6A to 6C are schematic diagrams showing the operation, in which the separate adapter 50 is attached and locked in the predetermined position on the endoscope control part 11, FIG. 6A showing the status before the adapter is attached, and FIGS. 6B and 6C showing the status after the adapter is locked. When the adapter 50 is to be attached to the endoscope control part 11, the entry part 54a of the endoscope locking part 54 is pushed sideways to fit it onto the cylindrical part 13. At this point, the entry part 54a of the endoscope locking part 54 deforms elastically, extending, and fits to the peripheral face of the cylindrical part 54. Also, in order to prevent the contact part 55 from interfering with the forceps valve 14, the endoscope locking part 54 is locked in the predetermined position by fitting it to a position that is higher than the predetermined position and then sliding it down, or inclining the adapter 50 when fitting it, or by carrying out a combination of these operations. As a result, as shown in FIG. 6C, the forceps valve 14 enters in and engages with the cutaway part 55a of the contact part 55 so that the adapter 50 is prevented from moving from the predetermined locking position and the position is determined.

Figure 7:
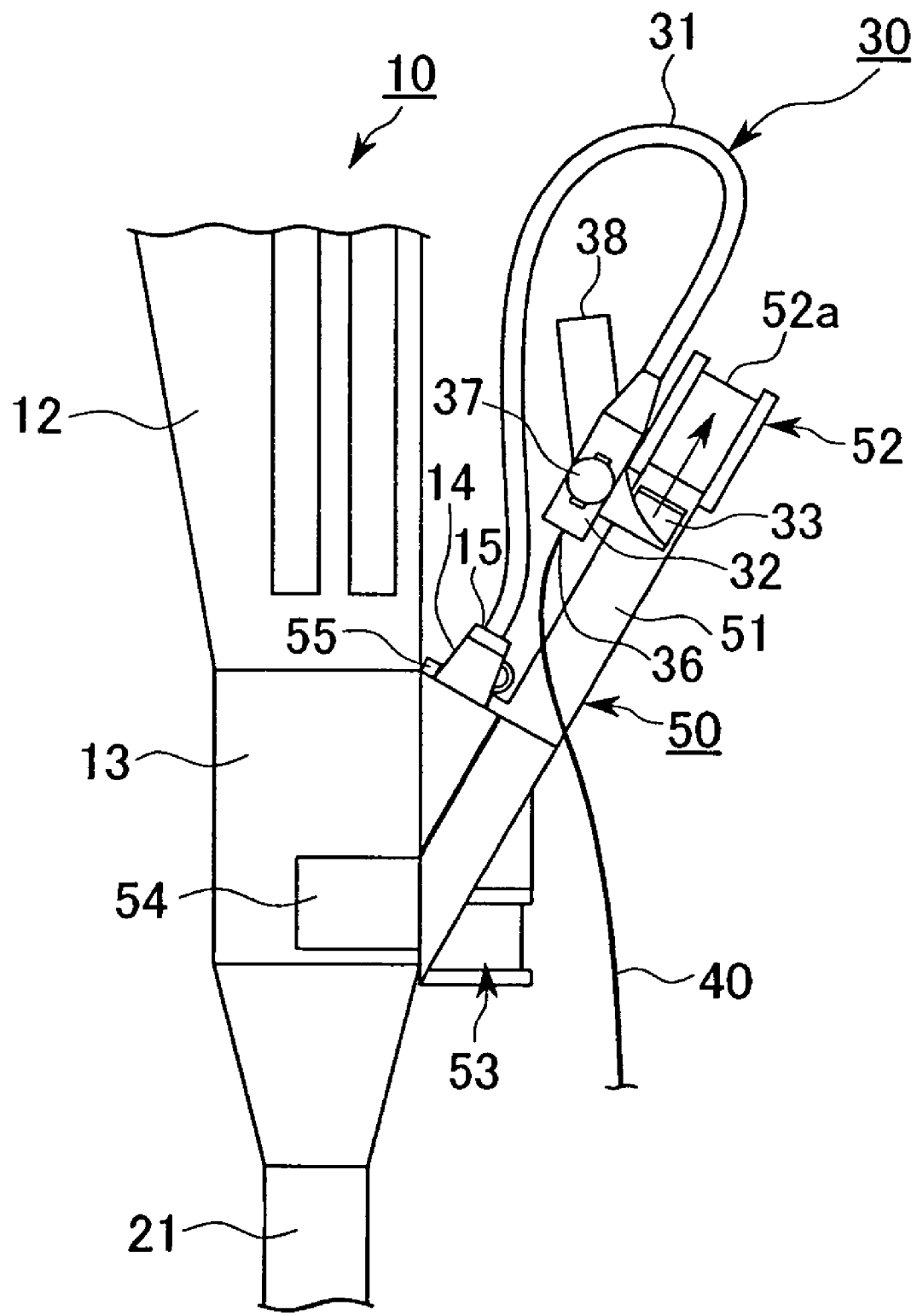
FIG. 7 is an explanatory diagram relating to the operation of treatment tool change in which the treatment tool control part of the catheter is attached to the endoscope adapter.
Figure 8A:
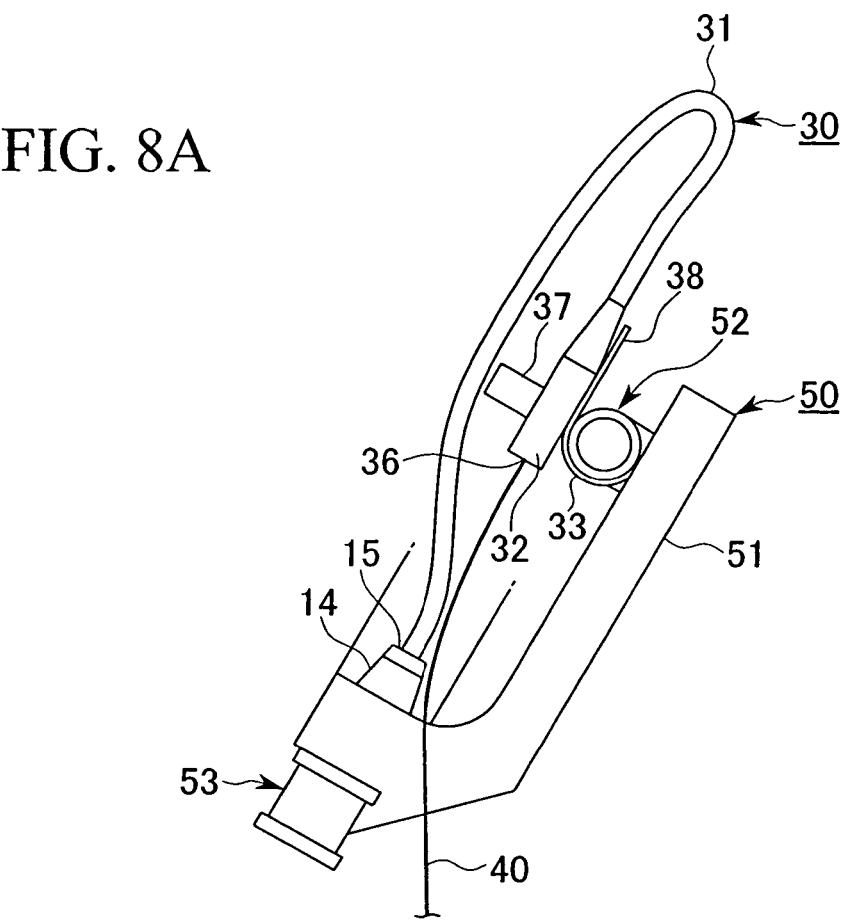
FIGS. 8A and 8B are explanatory diagram of the treatment tool change operation, FIG. 8A showing the status of the treatment tool control part of the catheter attached to the endoscope adapter, and FIG. 8B being a diagram showing the relative positions of a forceps entry aperture and a guidewire lumen entry aperture of the treatment tool control part.
Figure 8B:
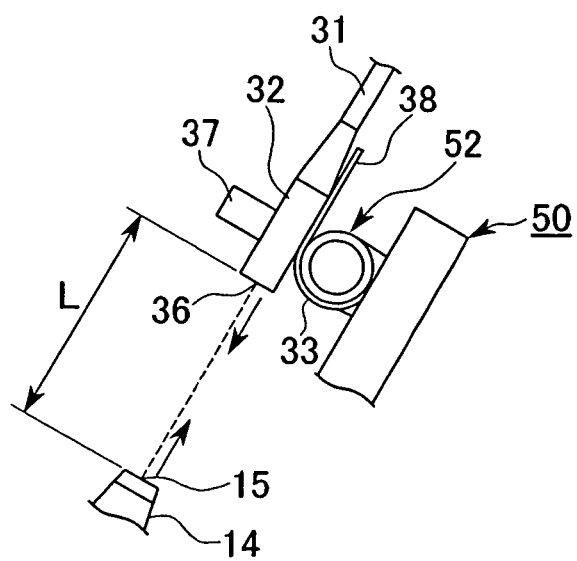
Figure 9:
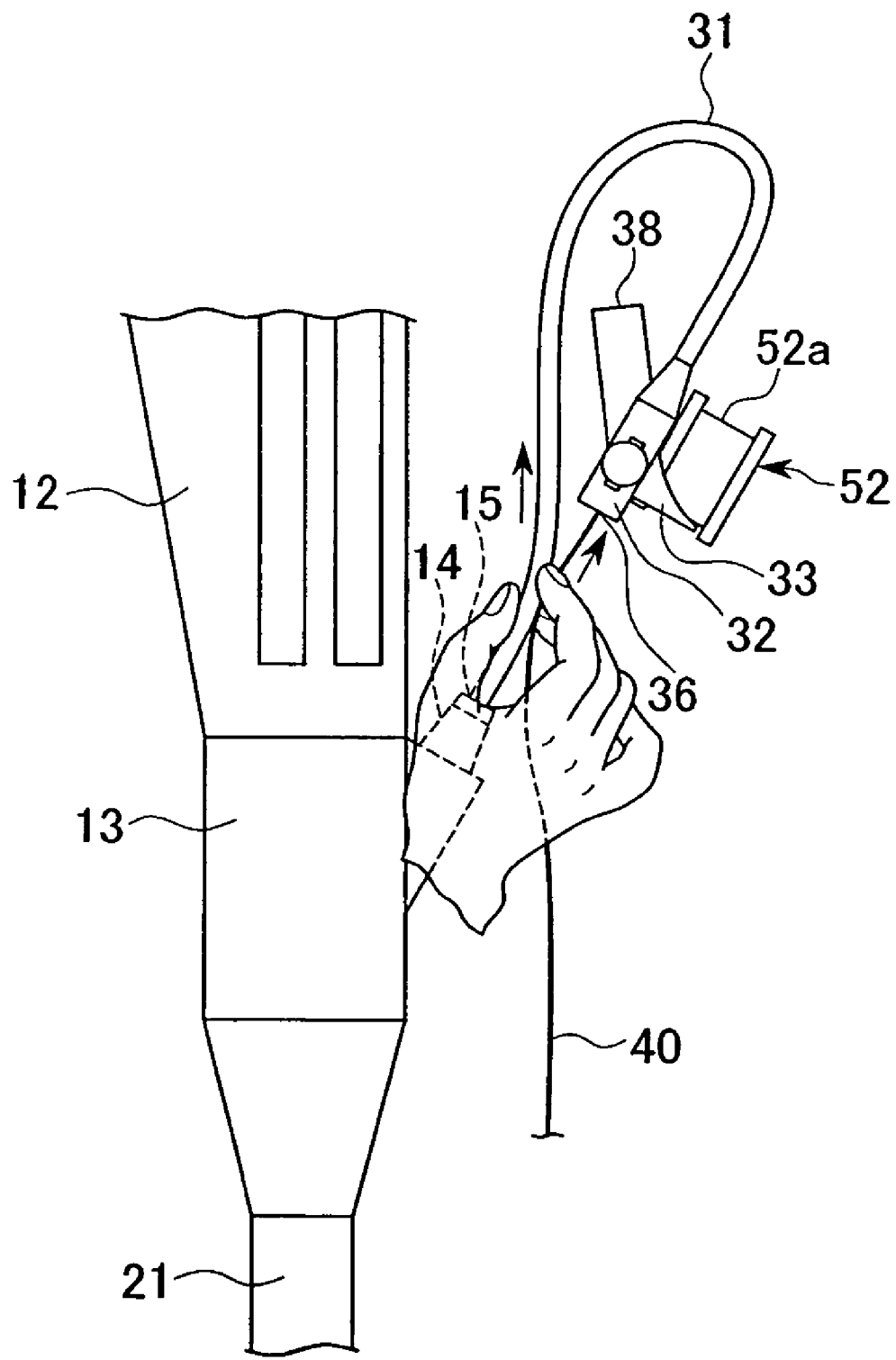
FIG. 9 is an explanatory diagram showing the treatment tool change operation, showing an aspect of the shaft of the catheter being pulled out.

Next, the operation of locking the treatment tool locking part 32 of the catheter 30 onto the adapter 50 that is locked in the predetermined position, in order to carry out the operation of changing treatment tools in which the catheter 30 that has completed treatment is changed for a new one, is described, with reference to FIG. 7 to FIG. 9. Also, it is assumed that the shaft 31 of the catheter 50, by known methods and operations, has passed through the forceps channel 25 from the entry aperture 15 of the forceps valve 14, along with the guidewire 40 that passes through the guidewire lumen 34, to be inserted to the desired position within the body cavity, and that the predetermined treatment has been completed.

When carrying out treatment tool change operation, firstly, the treatment tool locking part 32 of the catheter 30 is locked onto the first catheter locking part 52. In this locking operation, as shown in FIG. 7, the treatment tool control part 32 is turned around substantially 180 degrees, that is, the shaft 31 is U-turned and the segmental arch aperture 33a faces upward, and the treatment tool locking part 32 is lifted up in the direction indicated by the arrow from below the first catheter locking part 52 and fitted to the first cylindrical part 52a.

FIGS. 8A and 8B show the treatment tool control part 32 in locked status, and the entry aperture 15 of the forceps valve 14 and the guidewire lumen entry aperture 36 of the treatment tool control part 32 are positioned on substantially the same straight line opposing each other and they are separated only the predetermined distance L (see FIG. 8B) from each other. Accordingly, the shaft 31 extending upward out of the entry aperture 15 for the catheter 30 and the guidewire 40 extending downward out of the guidewire lumen entry aperture 36 are lined up parallel and next to each other on substantially the same straight line, that is, they are in a state in which the operator can hold both of them with one hand as shown in FIG. 9.

Therefore, when carrying out the operation of changing the treatment tool, it becomes possible for the operator to carry out the operation so that the operator uses one hand to hold the endoscope control part 11, and uses the other hand to grasp the shaft 31 and the guidewire 40 and feed them the same distance in the same direction.

In the example shown in FIG. 9, by carrying out an operation in which the shaft 31 and the guidewire 40 are grasped in one hand and moved upward in the direction indicated by the arrow, it becomes possible to carry out the operation in which the guidewire 40 is inserted and fed through the guidewire lumen entry aperture 36 while the shaft 31 is pulled out of the entry aperture 15 of the forceps valve 14.

As a result, since the shaft 31 is pulled out through the forceps channel 25, the length of the bend between the forceps valve 14 and the treatment tool control part 32 increases according to the length that has been pulled out (pulled out shift), and finally the end part 22 is pulled out of the entry aperture 15 of the forceps valve 14.

Meanwhile, since the treatment tool control part 32 is locked and unable to move and sufficient clearance is secured between the guidewire lumen 34 and the guidewire 40, the guidewire 40 is inserted into the guidewire lumen entry aperture 36 just as much as the shaft 31 is pulled out in its direction. That is, the guidewire 40 is inserted moving relative to the shaft 31. The insertion distance (insertion shift) accompanying with this movement corresponds to the length that the shaft 31 has been pulled out (pulled out shift), and accordingly, in actuality the insertion shift is absorbed by the pulled out shift so that there is no movement in the relative position of the end part 31a of the guidewire 40 and the channel exit aperture 23, and it is maintained in the position in which the operation commenced. Normally, during the operation, the endoscope end is positioned at a certain place within the body. Therefore, the end part 31a of the guidewire 40, of which the relative position to the channel exit aperture 23 of the endoscope end is locked, is maintained at a certain position within the body.

Therefore, when carrying out the operation of changing the catheter 30, it becomes possible for the same kind of operation as the two-person operation by trained persons, in which the pulled out shift and the insertion shift are made to be the same, to be carried out easily and surely, and thus, the catheter 30 can easily and quickly be pulled out leaving the guidewire 40 in the forceps channel 25.

Furthermore, as with the abovementioned operation of pulling out the catheter 30, in the operation of inserting a new replacement catheter to be used, if it is moved counter to the direction of FIG. 9, that is if they are moved the same amount in the direction in which the shaft 31 is inserted into the entry aperture 15 while the guidewire 40 is pulled out from the guidewire lumen entry aperture 36, then a single operator can easily and quickly carry out insertion of the catheter 30. In this case, after the end part of the guidewire 40 coming out of the entry aperture 15 of the forceps valve 14 is inserted through the guidewire lumen exit aperture 35 and is passed completely through the guidewire lumen 34, the treatment tool control part 32 may be locked onto the first catheter locking part 52 of the adapter 50.

Incidentally, in view of controllability and frequency of the insertion and pulling out operations, it has been confirmed from various examinations that the predetermined distance L mentioned above is most preferably configured to be approximately 10 cm when the shaft 31 (inner diameter of the guidewire lumen approximately 1 to 1.2 mm) and the guidewire 40 (outer diameter approximately 0.9 cm) that are used for general endoscopic treatment are used.

Specifically, when the configuration of the distance L is too long, the guidewire 40 in particular bends and smooth insertion becomes difficult and controllability declines noticeably. On the other hand, when the configuration of the distance L is too short, the length of insertion or pulling out at single operation (shift) becomes short so the number of times the operation must be repeated in order to achieve the required shift increases.

Figure 10A:
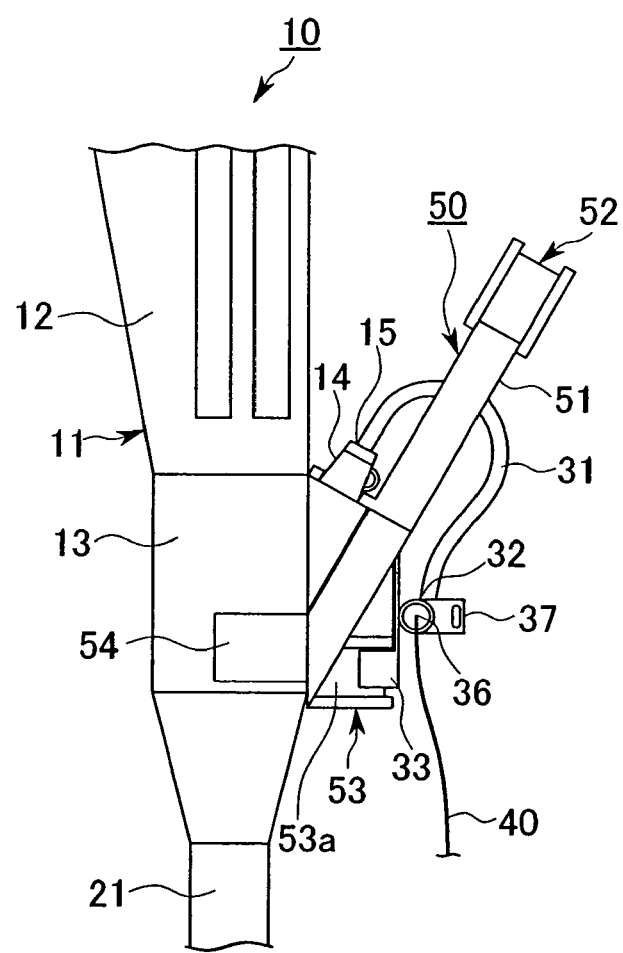
FIGS. 10A and 10B are explanatory diagrams showing the status of normal operation, FIG. 10A being a front view showing the status of the treatment tool control part of the catheter locked on the endoscope adapter, and FIG. 10B being a right side view thereof.
Figure 10B:
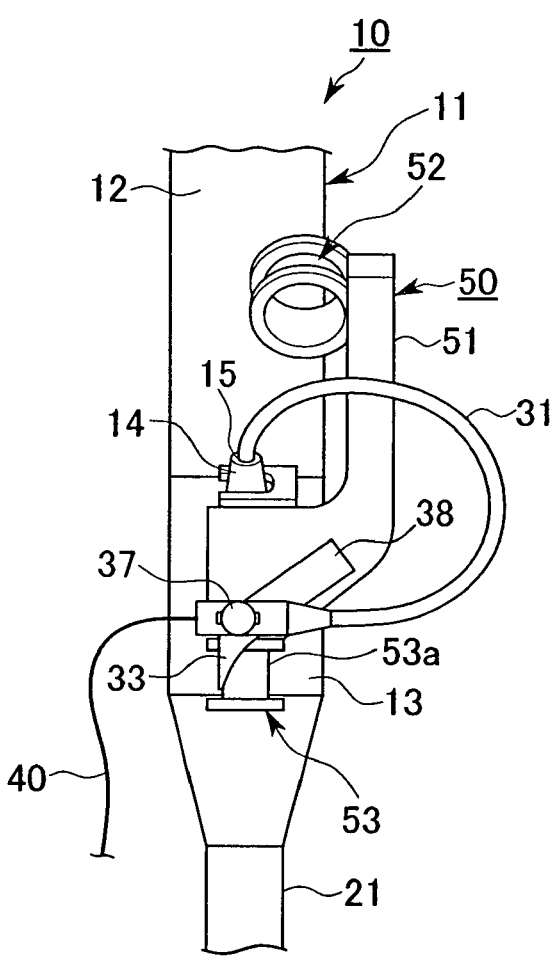

As mentioned above, as long as the adapter 50 has the first catheter locking part 52, the catheter change operation can be made easy. However, it is preferable to also have the second catheter locking part 53 in addition to the first catheter locking part 52 mentioned above. This second catheter locking part 53 is used when carrying out the normal operation of inserting the guidewire 40 into the target position within the body cavity, and this is described making reference to FIGS. 10A and 10B.

In this case, the treatment tool locking part 33 of the treatment tool control part 32 is fitted and locked to the second cylindrical part of the second catheter locking part 53. In this locking position, the direction of the guidewire lumen entry aperture 36 intersects the direction of the exit aperture 15 of the forceps valve 14, so that the shaft 31 and guidewire 40 are not next to each other in a substantially parallel fashion as in the abovementioned change operation, and thus, the shaft 31 does not interfere with the insertion amount adjustment operation.

Furthermore, the movement direction of the guidewire 40 inserted or pulled out through the guidewire lumen entry aperture 36 by the operator is substantially the same direction as the direction of operation of the guidewire whose end part goes in and comes out through the guidewire lumen exit aperture 35, so that the insertion amount adjustment can easily be done without creating sensory discomfort.

Thus, the treatment tool control part 32 of the catheter 30 can be locked even in normal operations, so that the operator can hold the endoscope control part 11 in one hand and control the guidewire 40 with the other hand and the insertion amount adjustment can easily be carried out.

In the embodiment described so far, the adapter 50 that locks the catheter 30 onto the predetermined position can be freely detached from the cylindrical part 13 and so forth of the endoscope control part 11, but it may be integrated with the endoscope control part 11 and so forth in other embodiments. To give a concrete example, it may be constructed having it bifurcated from the cylindrical part 13, that is, having a rod-shaped connection part 51 provided for which the part corresponding to the endoscope locking part 54 is integral with the cylindrical part 13, and this connection part 51 has a first catheter locking part 52, or it may be constructed having the first catheter locking part 52 and a second catheter locking part 53 provided. In this case, as it becomes a fixed construction, the member corresponding to the contact part 55 of the position determination device is not required, and also, the first catheter locking part 52 and the second catheter locking part 53 may be provided with respective independent connection parts and locked onto the appropriate place on the side of the endoscope 10.

Next, a modification example of the adapter 50 is described as a second embodiment making reference to FIG. 11A to FIG. 14. Also, the same reference symbols are assigned to the same parts, such as the adapter 50 shown in FIG. 2, in the diagrams used for description so far and their detailed descriptions are omitted.

The adapter 50A of this embodiment is different in respect to the construction of the connection part 51 shown in FIG. 2 and that the second catheter locking part 53 is not provided, and as for the connection part, a pin 56 connects a first connection part 51A (first rod-shaped member) and a second connection part 51B (second rod-shaped member) and allows them circular movement.

Figure 11A:
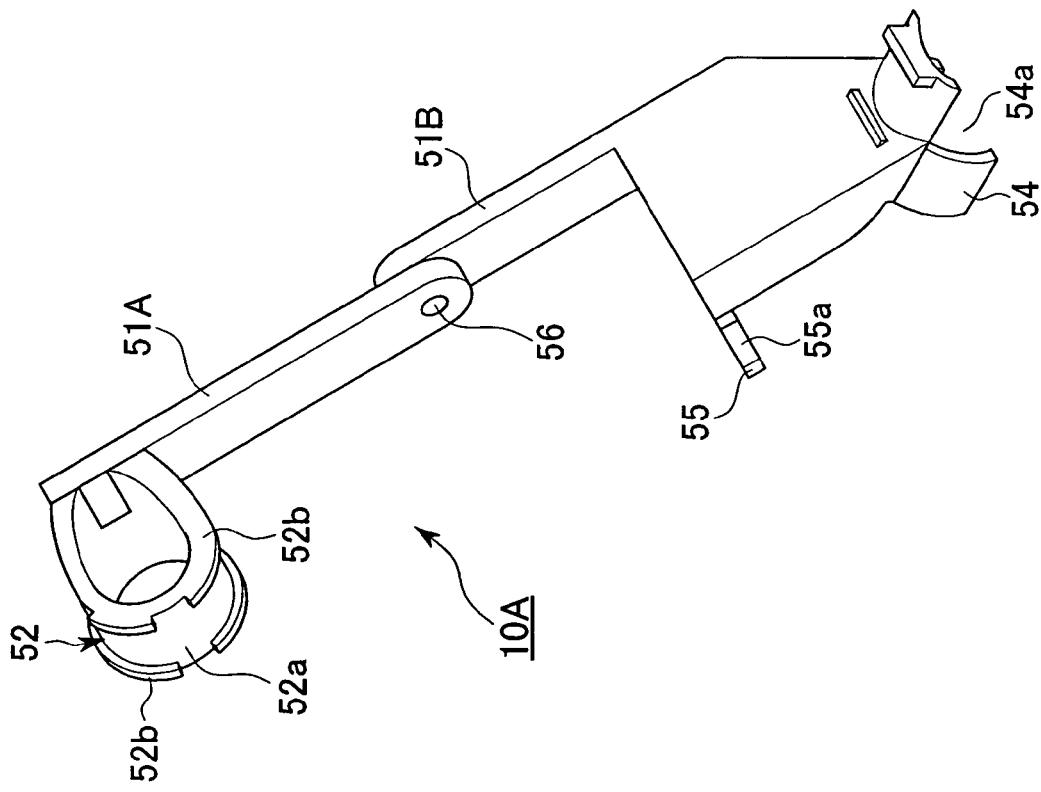
Figure 12:
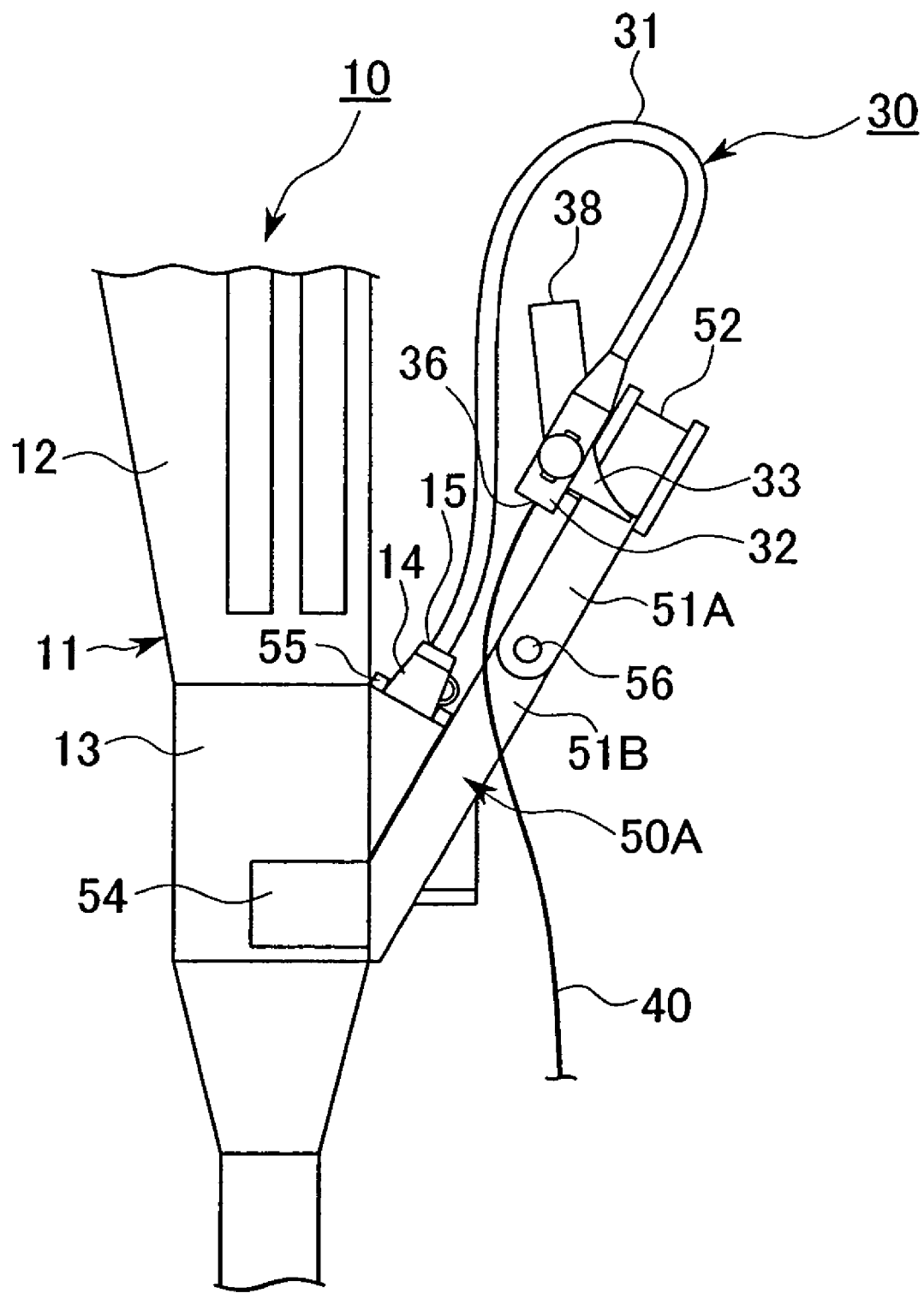
FIG. 12 is an explanatory diagram showing the situation of the operation of changing treatment tools being carried out with the endoscope adapter of FIG. 11A attached to the endoscope.

The adapter 50A constructed in this way has a first catheter locking part 52 on the top end side of the first connection part 51A. This first catheter locking part 52 is made to be able to correspond to two locking positions mentioned above with one part to be locked onto. That is, as shown in FIG. 11A and FIG. 12, when used maintaining the first connection part 51A and the second connection part 51B straight, it is practically the same as the adapter 50 in FIG. 2 except that the second catheter locking part 53 is not present. Therefore, by attaching the adapter 50A in this state to the cylindrical part 13, it can be used for the operation of changing treatment tools.

Furthermore, as techniques for maintaining the first connection part 51A and the second connection part 51B straight or bent, commonly acknowledged techniques such as using frictional force may be employed.

Figure 11B:
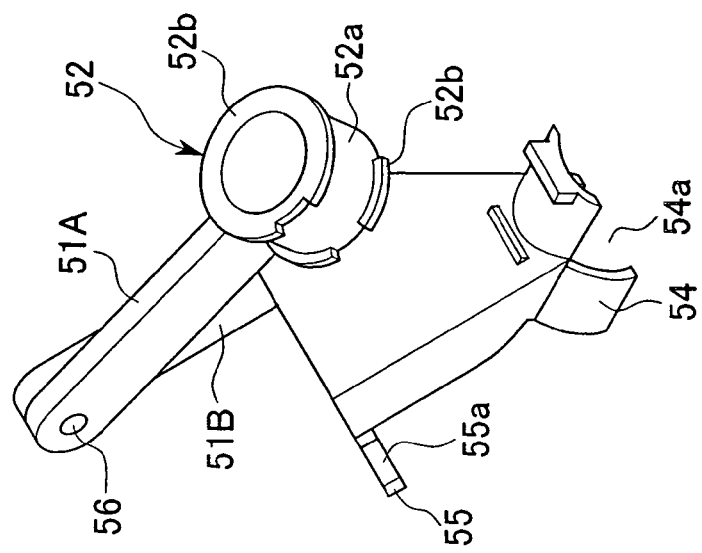
FIGS. 11A and 11B are perspective views showing a second embodiment of an endoscope adapter, FIG. 11A showing a status of being maintained in a straight line, and FIG. 11B showing shows a status of being bent.
Figure 13:
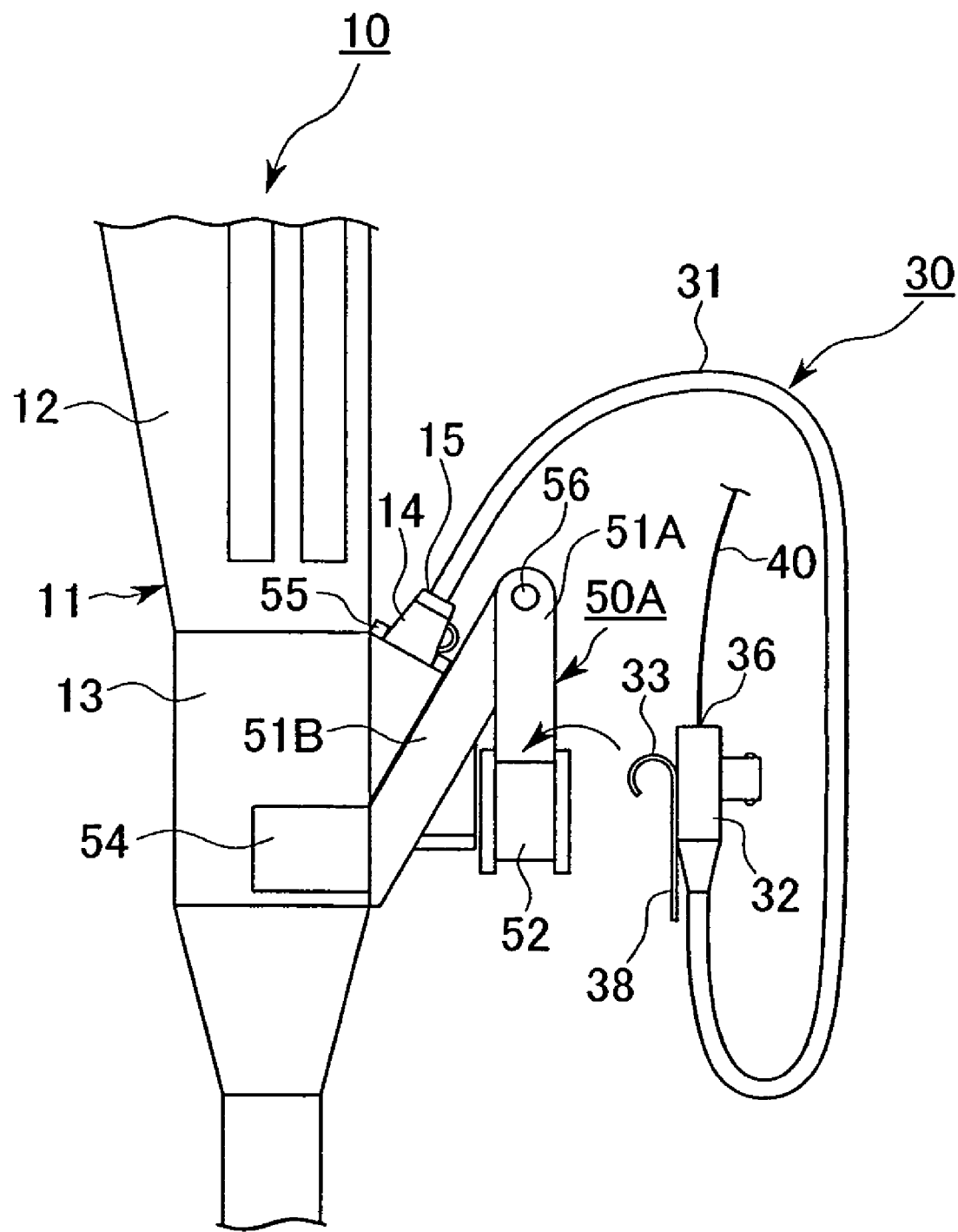
FIG. 13 is an explanatory diagram relating to the operation for the normal operation in which the endoscope adapter of FIG. 11B is attached to the endoscope, and the treatment tool control part of the catheter is attached.
Figure 14:
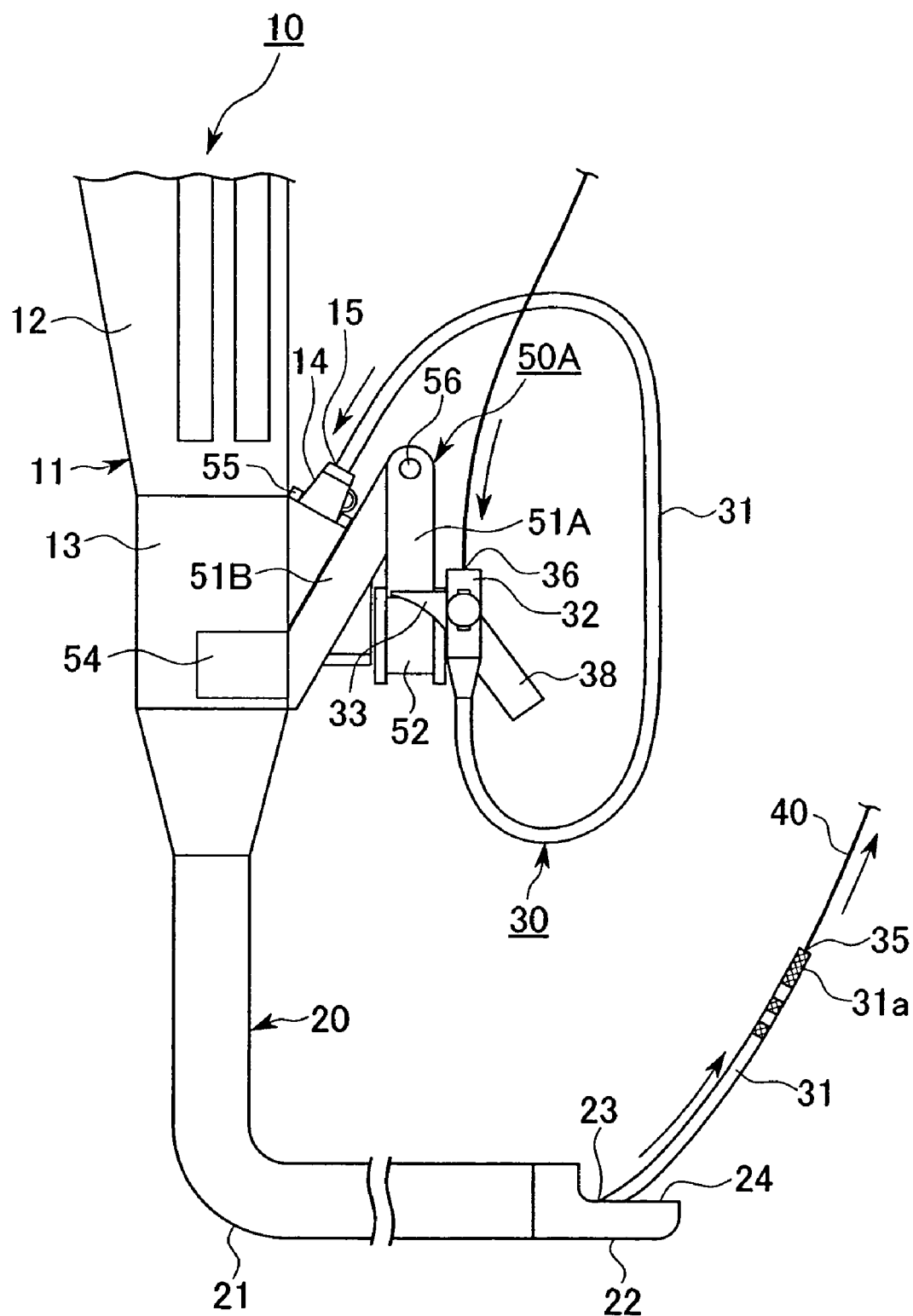
FIG. 14 is an explanatory diagram showing the situation in which the endoscope adapter of FIG. 11B is attached to the endoscope and a normal operation is being carried out.

Next, in the bent status shown in FIG. 11B, the catheter locking part 52 rotates downward along with the first connection part 51A with the pin 56 as a fulcrum, and thus, it can carry out the same function as that of the second catheter locking part 53 of the adapter 50 in FIG. 2 mentioned above. Specifically, as shown in FIG. 13 and FIG. 14, when the U-shaped part 33 of the treatment tool control part 32 is fitted and locked to the first catheter locking part 52 of the first connection part 51A maintained in a bent state, the guidewire lumen entry aperture 36 comes to face a direction that intersects the exit aperture 15 of the forceps valve 14. Thus, the shaft 31 and the guidewire 40 are not next to each other substantially in parallel as when carrying out the changing operation mentioned above, and also, the direction of movement of the guidewire 40 that the operator inserts or pulls out through the guidewire lumen entry aperture 36, becomes substantially the same direction as the direction of operation of the guidewire, in which its end part goes in and out through the guidewire lumen exit aperture 35, so that the insertion amount adjustment can easily be done without creating sensory discomfort.

Incidentally, the adapter 50A mentioned above has a construction which allows the connection part to be bent around the pin 56, and the single catheter locking part can be shared for two operations, however, besides this, various kinds of modification example, such as a construction sharing a single catheter locking part by providing the endoscope locking part to two places, are possible. Also, the first catheter locking part 52 and the second catheter locking part 53 may be attached to the connection part 51 allowing them rotation so that their angles can be adjusted appropriately. Moreover, for the adapter 50A just described, it may be constructed so that the appropriate place for the second connection part is fixed to the endoscope control part 11 side.

Figure 15:
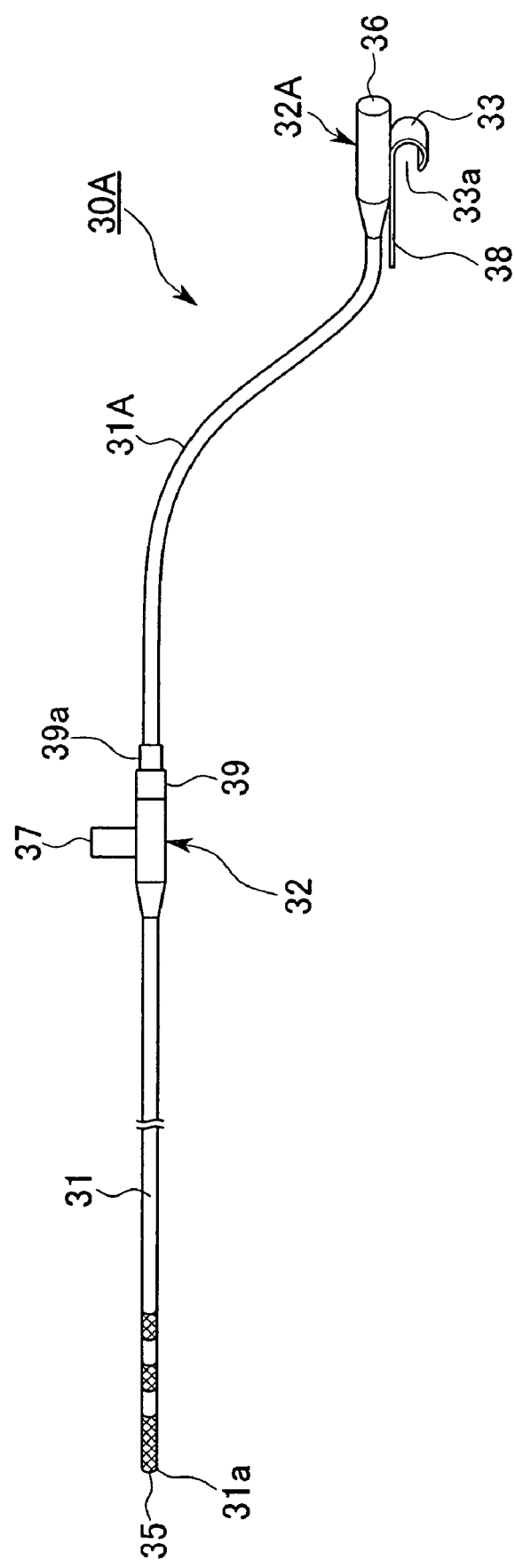
FIG. 15 is a perspective view showing the construction of a catheter relating to a third embodiment of the present invention.
Figure 16:
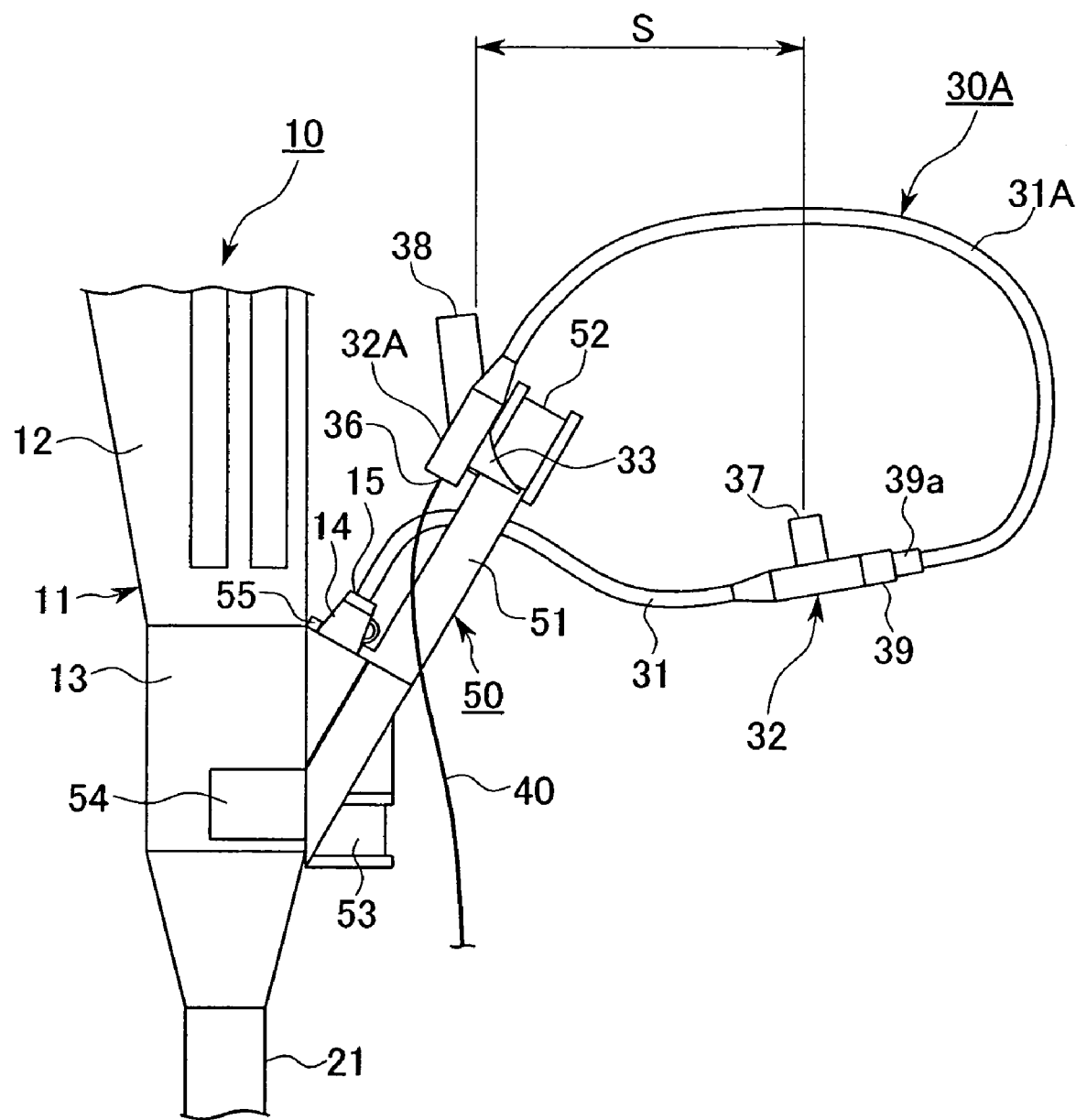
FIG. 16 is an explanatory diagram showing the situation of the catheter of FIG. 15 being locked on the endoscope adapter during a treatment tool change operation.

Next, a third embodiment of the present invention is described making reference to FIG. 15 and FIG. 16. Also, the same reference symbols are assigned to the same parts, such as the catheter 30, in the diagrams used for description so far, and their detailed descriptions are omitted.

In this embodiment, the construction of the catheter 30A treatment tool is such that it has a shaft extension part 31A connected to the guidewire entry aperture 36 of the treatment tool control part 32 via a watertight cock which is a connection member having a watertight device. In this case, the forceps valve side end part of the shaft 31 having a normal length is connected to the one end of the watertight cock 39, and also, a shaft extension part 31A is connected to the other end of this watertight cock 39.

The watertight cock 39 is a well known one which compresses an elastic tube by screwing in a pressure cap 39a, and maintains water tightness by sealing the inner peripheral face of the elastically deformed elastic tube to the guidewire 40 passing through its interior, and is disclosed in FIG. 2 and so forth of the Japanese Unexamined Patent Application, First Publication No. H08-187292, for example. A fluid feeding cap 37 for injecting contrast medium is provided on this watertight cock 39, but this fluid feeding cap 37 is provided on the guidewire lumen exit aperture 35 side of the elastic tube that maintains water tightness.

Also, a treatment tool control part 32A, having the same construction as the treatment tool control part 30 of the embodiment mentioned above except that the fluid feeding cap 37 has been removed from it, is provided and connected to the other end of the shaft extension part 31A.

With a catheter 30A having the construction just described, sufficient distance S for two persons to operate can be secured between the treatment tool control part 32A of the catheter 30A locked on the endoscope 10 and the fluid feeding cap 37 provided on the watertight cock 39. Specifically, since there is sufficient distance S between the operator who controls the endoscope 10 and a nurse who injects contrast medium through the fluid feeding cap 37, their respective operations can be carried out surely without interfering with each other. Also, it goes without saying that the distance S can be adjusted by appropriately changing the length of the shaft extension part 31A. Incidentally, the watertight cock 39 is to prevent the contrast medium fed through the fluid feeding cap 37 from flowing back to the side close to the hand and squirting out through the guidewire lumen entry aperture 36, by screwing in the pressure cap 39a, but if a lumen for injecting contrast medium, for example, is independently provided in addition to the guidewire lumen 34, then when the shaft extension part 31A is only connected to the guidewire lumen 34, the watertight cock is not required as the contrast medium injected through the fluid feeding cap 37 would not flow back through the shaft extension part 31A.

Next, a fourth embodiment that relates to the present invention is described making reference to FIG. 17 to FIG. 27. Also, the same reference symbols are assigned to the same parts in the diagrams used for description so far, and their detailed descriptions are omitted.

An adapter 50B that relates to the present embodiment is constructed with an integrated connection part 51C as with the adapter 51A which relates to the first embodiment, but the present embodiment differs from other embodiments mentioned above with respect to the following points.

Figure 17:
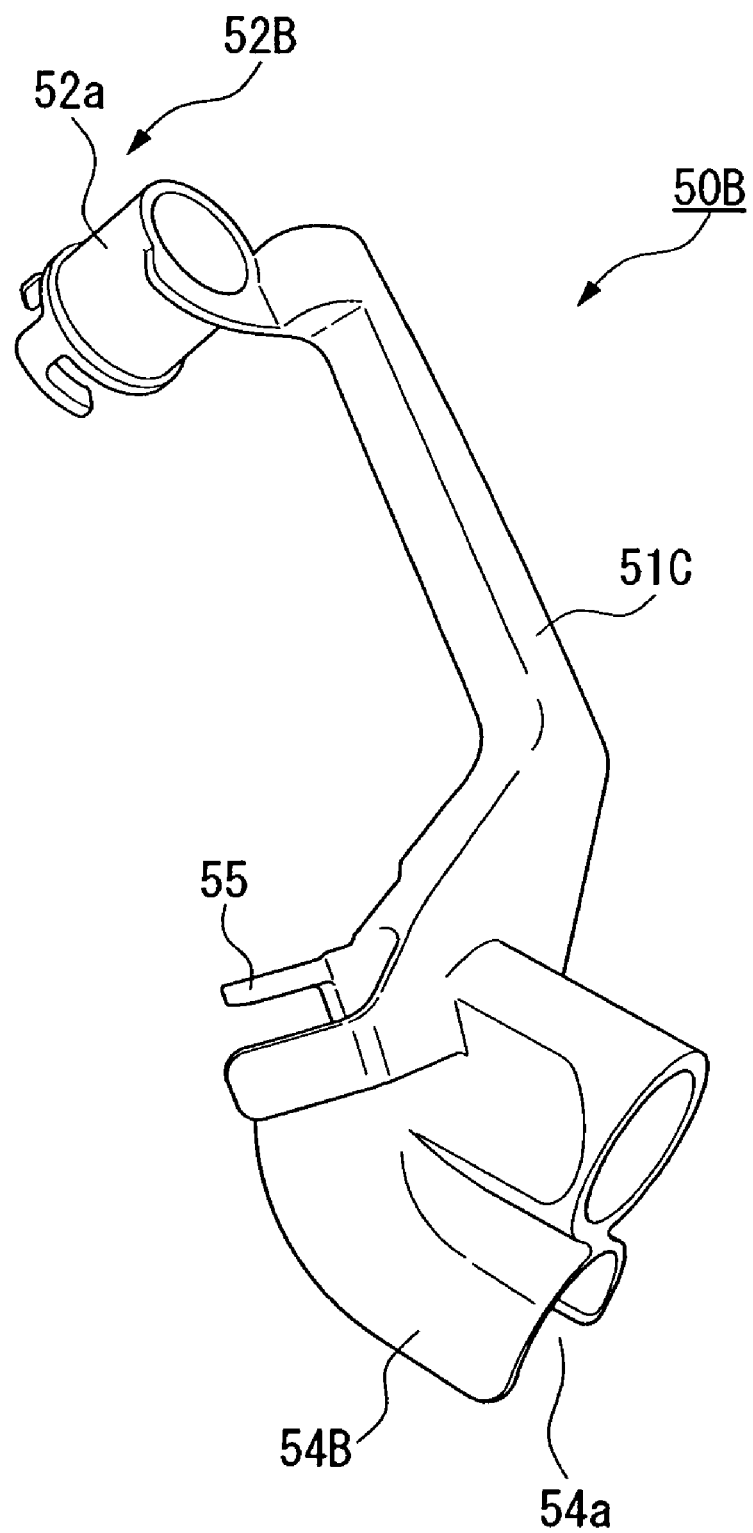
FIG. 17 is a perspective view showing a configuration example of an endoscope adapter according to a fourth embodiment of the present invention.
Figure 18:
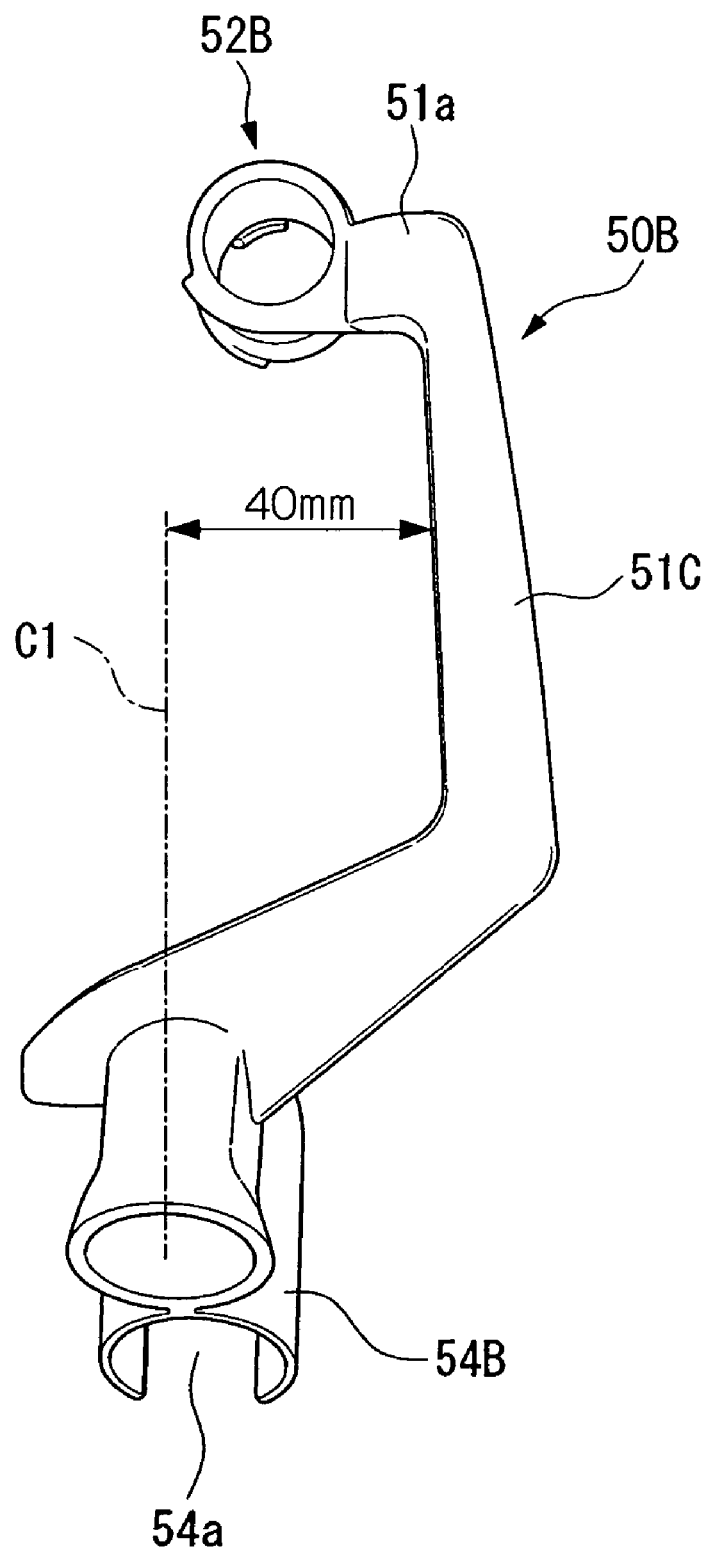
FIG. 18 is a plan view showing the configuration example of the endoscope adapter according to the fourth embodiment of the present invention.

As shown in FIG. 17, an endoscope locking part 54B is in a substantially half cylindrical shape allowing it to be attached to the cylindrical part 13, and the edge part of the endoscope locking part 54B has been chamfered roundly. As shown in FIG. 18, the connection part 51C is off-center and arranged in a position 40 mm distant from the central axis C1 of the endoscope locking part 54B, and is formed extending along the central axis C1. The top end 51a of the connection part 51C is formed to bend towards the central axis C1.

A first catheter locking part 52B, which also acts as a second catheter locking part in the same way as the adapter 50A that relates to the second embodiment, is arranged on the top end part 51a of the connection part 51C.

Figure 19:
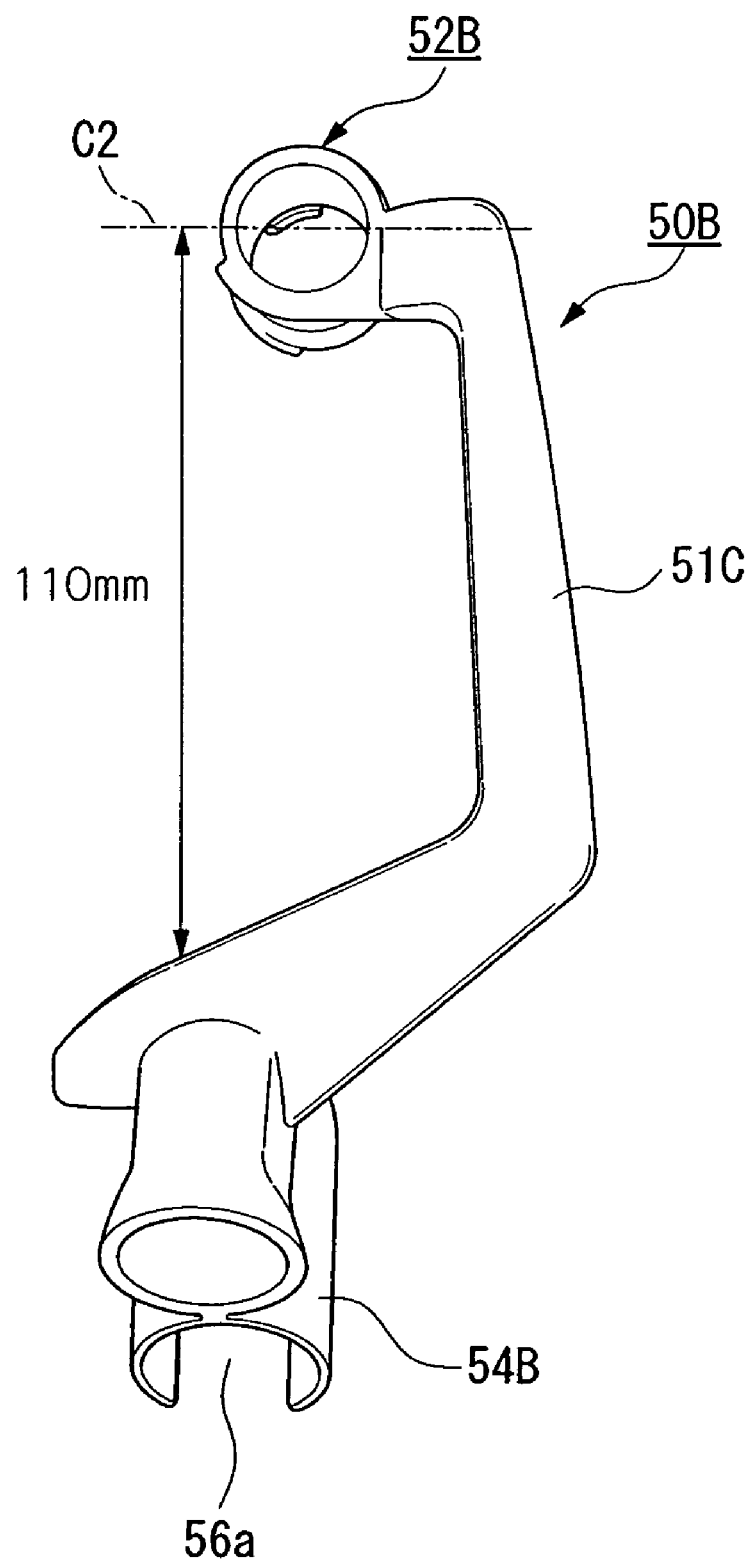
FIG. 19 is a plan view showing the configuration example of the endoscope adapter according to the fourth embodiment of the present invention.

As shown in FIG. 19, this first catheter locking part 52B is arranged in a position where the center of the first cylindrical part 52a is 110 mm distant from the endoscope locking part 54B.

Figure 20:
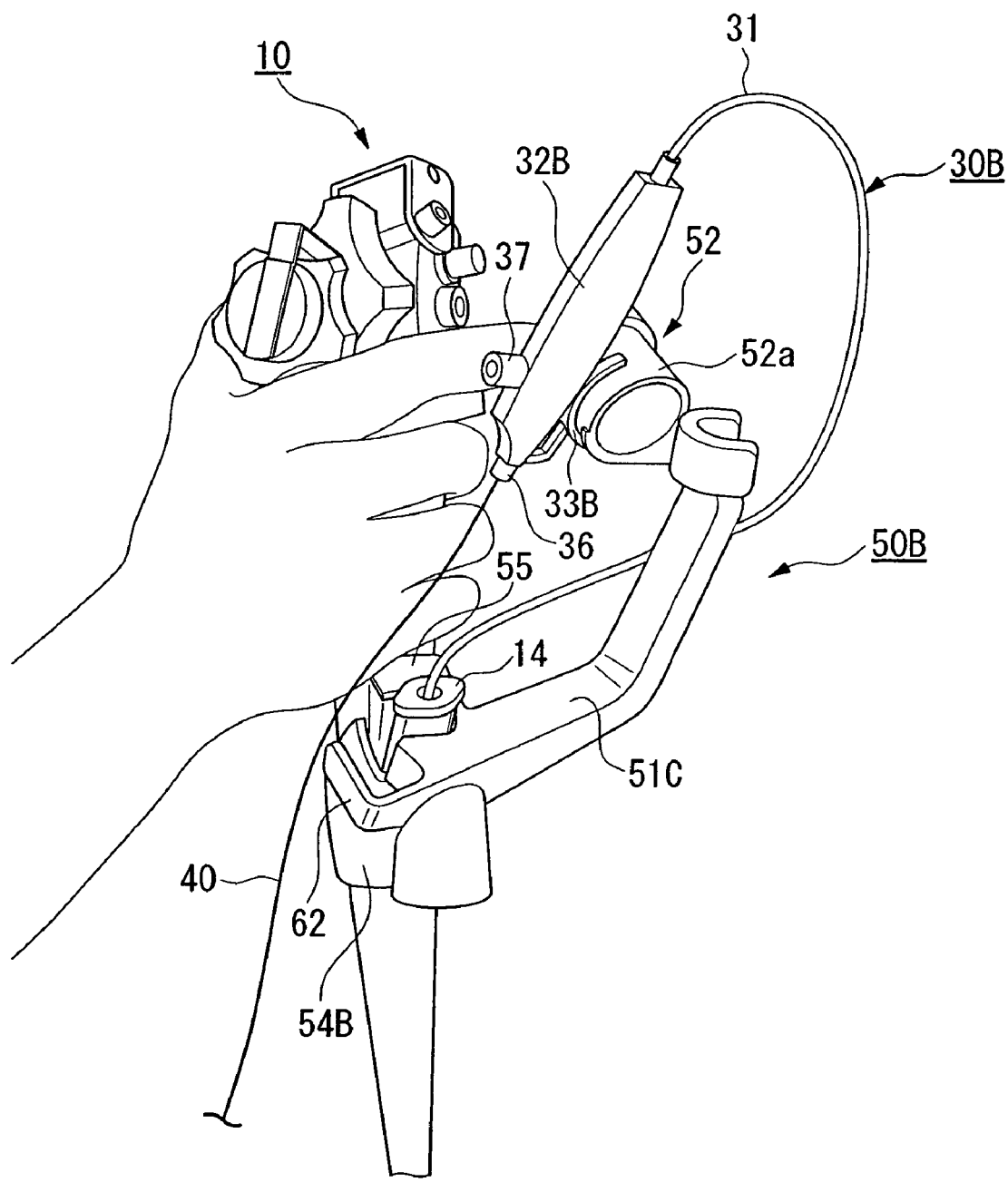
FIG. 20 is an explanatory diagram showing a first predetermined position in the operation of changing treatment tools according to the fourth embodiment of the present invention.
Figure 21:
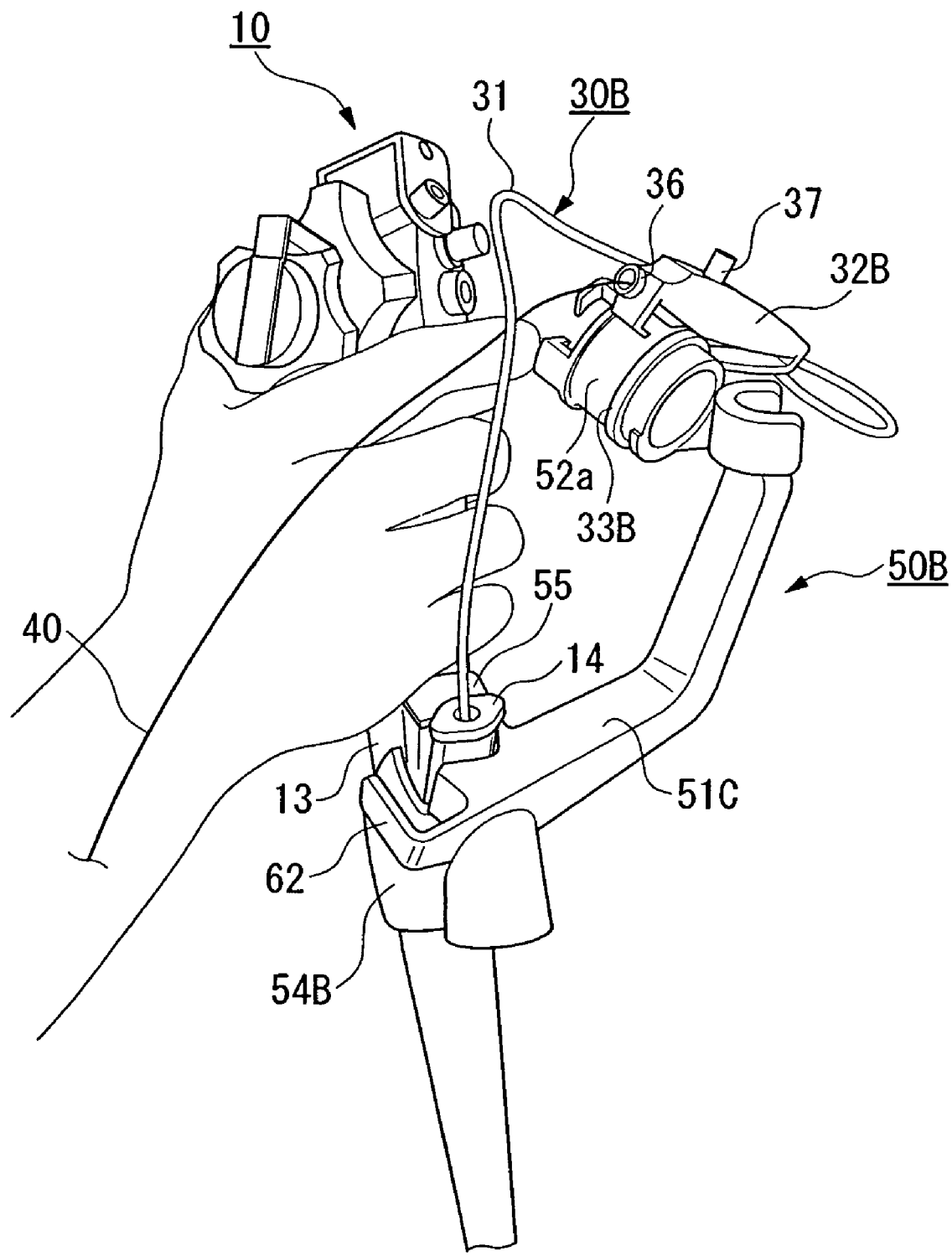
FIG. 21 is an explanatory diagram showing a second predetermined position in the operation of changing treatment tools according to the fourth embodiment of the present invention.

The first cylindrical part 52a of the first catheter locking part 52B has a frictional surface which allows sliding when a U-shaped part 33B of the treatment tool control part 32B is attached, and the first predetermined position shown in FIG. 20 and the second predetermined position shown in FIG. 21 can be selected by sliding the U-shaped part 33B over the circumference of the first cylindrical part 52a.

Figure 22:
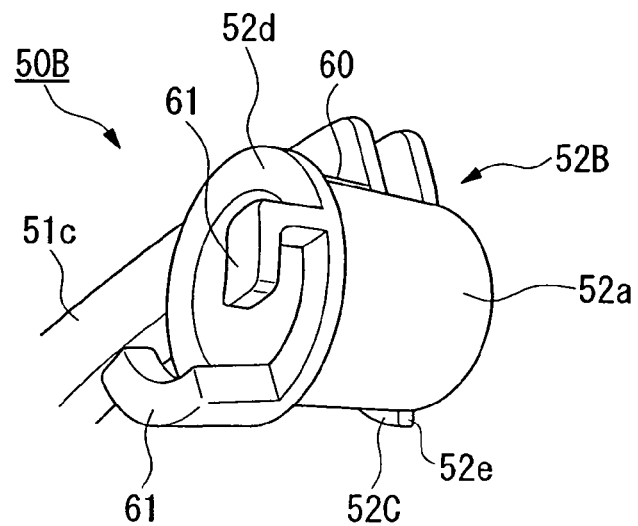
FIG. 22 is an enlarged view of a relevant part showing the endoscope adapter according to the fourth embodiment of the present invention.

In order to determine the position so that at the second predetermined position the guidewire 40 is not facing in the direction of the operator operating the endoscope 10 through the guidewire lumen entry aperture of the treatment tool control part 32B, or in the direction of the patient, a regulation member 60 for determining the position in which the U-shaped part 33B can be engaged, is arranged on the first cylindrical part 52a as shown in FIG. 22. Consequently, when it is attached to the first cylindrical part 52a, the U-shaped part 33B can slide more than 90 degrees on the first cylindrical part 52a until the end part 33b of the U-shaped part 33B makes contact with the regulation part 60.

Flange parts 52c and 52d are provided on both end sides of the first cylindrical part 52a. A cutaway part 52e is provided on one part of the flange part 52c. The edge parts of the flange parts 52c and 52d have been chamfered roundly.

Figure 23:
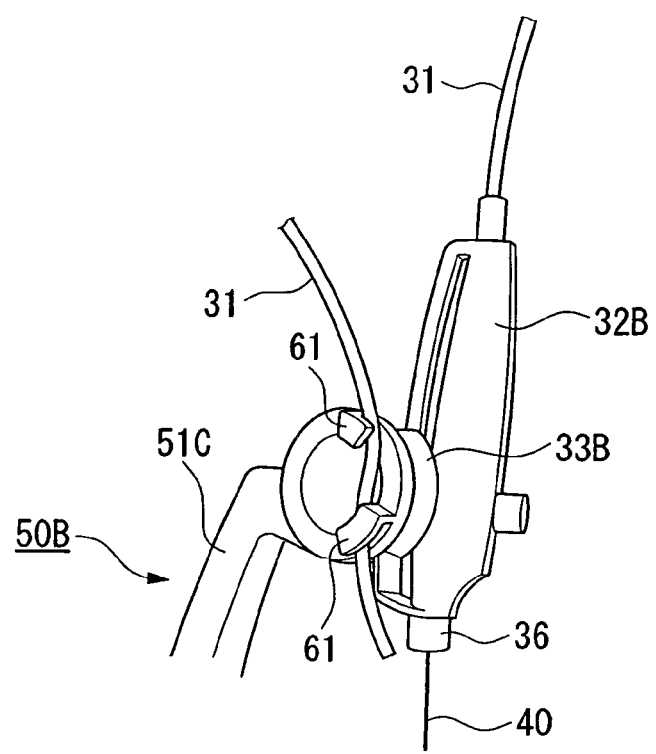
FIG. 23 is an explanatory diagram relating to the operation of changing treatment tools according to the fourth embodiment of the present invention.

Two first hooks 61 are provided on the flange part 52d side end face of the first catheter locking part 52B, protruding from the side face along the circumferential direction of the first cylindrical part 52a. As shown in FIG. 23, these first hooks 61 are arranged in the positions where the shaft 31 or the guidewire 40 can be engaged making the guidewire 40 and the shaft 31 substantially parallel when the adapter 50B is attached to the cylindrical part 13.

Figure 24:
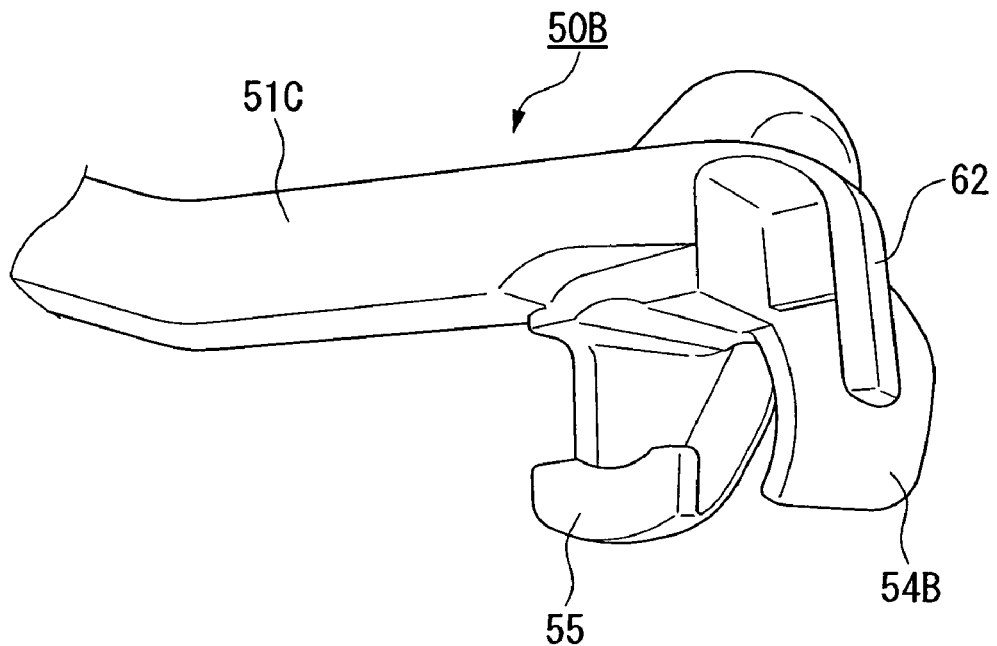
FIG. 24 is an enlarged view of a relevant part showing the endoscope adapter according to the fourth embodiment of the present invention.

As shown in FIG. 24, a second hook 62, which engages the guidewire 40 in order to position the shaft 31 and the guidewire 40 parallel to each other to make them easy to grip, maintaining the direction of the shaft 31 engaged by the first hooks 61, is provided near the endoscope locking part 54B.

Figure 25:
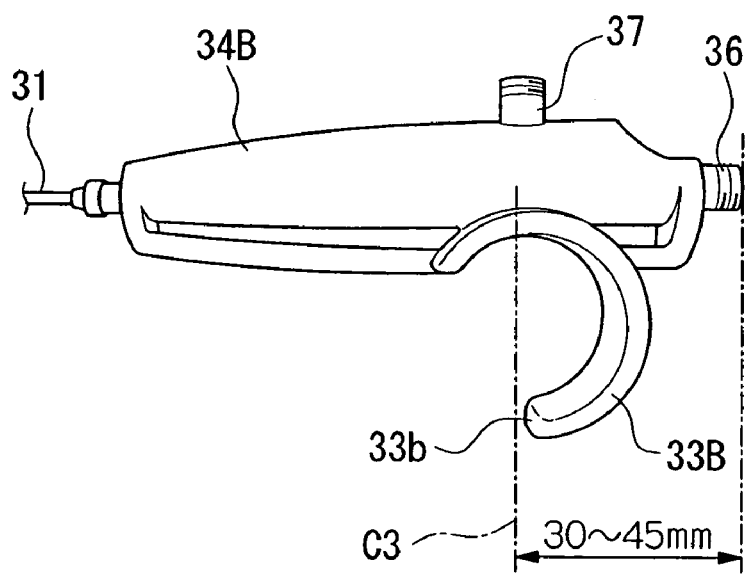
FIG. 25 is a side view showing the treatment tool control part of the catheter relating to the fourth embodiment of the present invention.

Meanwhile, as shown in FIG. 25, the treatment tool control part 32B of the catheter 30B that relates to the present embodiment is constructed so that the distance between the attaching position C3 of the U-shaped part 33B and the guidewire lumen entry aperture 36 is from 30 mm to 45 mm.

Figure 26:
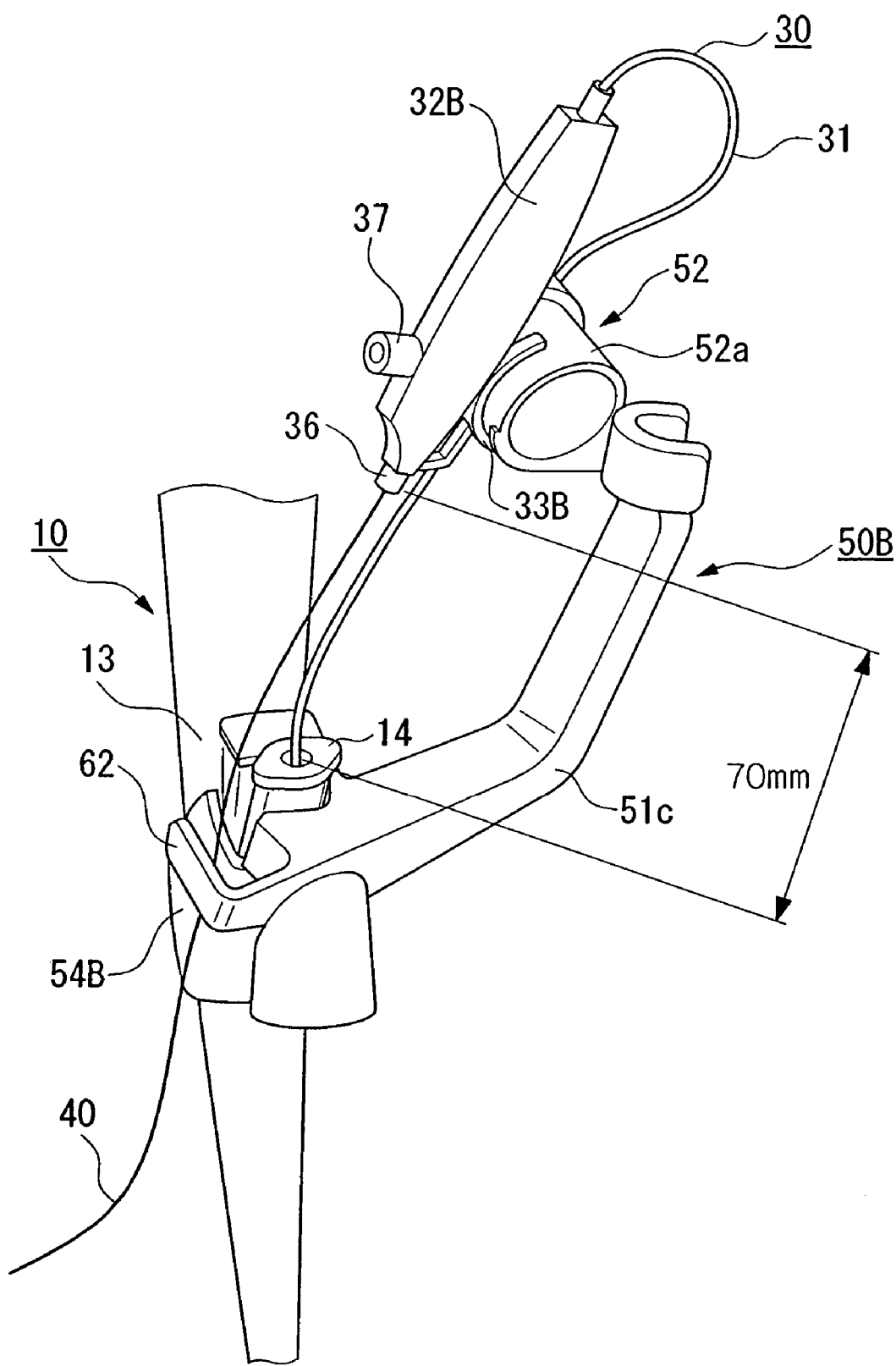
FIG. 26 is an explanatory diagram showing the first predetermined position in the operation of changing treatment tools according to the fourth embodiment of the present invention.

The first catheter locking part 52B is arranged on the connection part 51B so that the distance between the guidewire lumen entry aperture 36 and the forceps valve 14 is 70 mm, as shown in FIG. 26, when this U-shaped part 33B of the treatment tool control part 32B is locked on the first catheter locking part 32B.

The edge part of the U-shaped part 33B is chamfered roundly.

Figure 27:
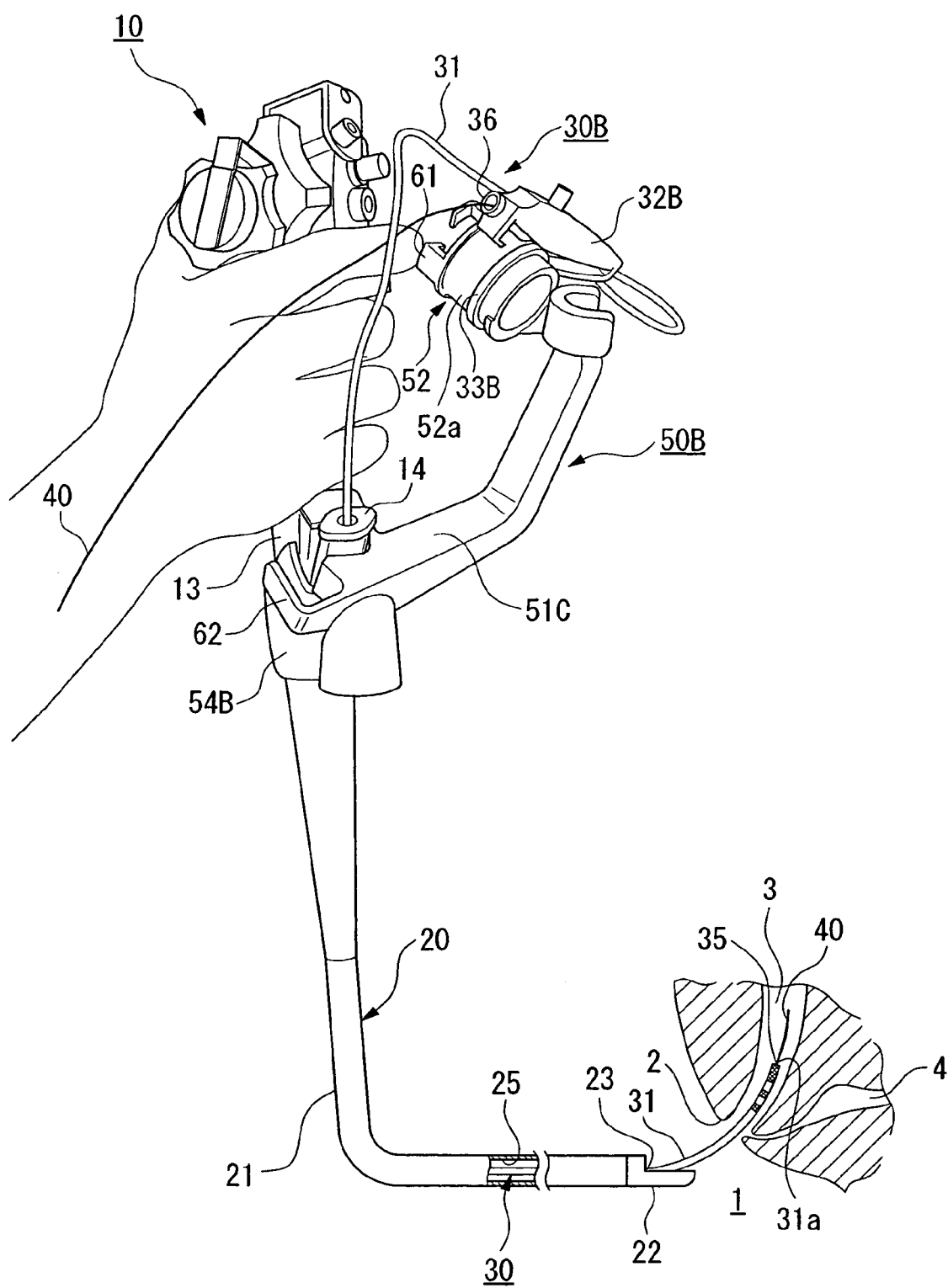
FIG. 27 is a diagram showing an aspect of the endoscope adapter being used in combination with an endoscope and a catheter, as a fourth embodiment of the endoscope adapter according to the present invention.

The operation of changing treatment tools with the adapter 50B that relates to the present embodiment constructed as mentioned above can also be carried out in a similar manner to the other embodiments described above, and treatment by the catheter 30B can be carried out as shown in FIG. 27.

Here, the connection part 51C is arranged to be off-set 40 mm from the endoscope locking part 54B as mentioned above, and since the distance between the endoscope locking part 54B and the first catheter locking part 52B is made to be 110 mm, when the treatment tool control part 32B is attached to the first cylindrical part 52a and it is set to the first predetermined position, the hand can enter easily into the off-set part mentioned above, and the operation area when controlling the shaft 31 and the guidewire 40 to move back and forth can definitely be made bigger than in the case of other embodiments mentioned above.

Furthermore, since the first catheter locking part 52B also serves as the second catheter locking part, the first predetermined position and the second predetermined position can easily be switched by simply sliding the U-shaped part 33B on the circumference of the first cylindrical part 52a. In this case, the treatment tool control part 32B does not need to be detached from the adapter 50B, so that the operator can concentrate on the image on the monitor, not shown in the diagram, without being distracted by the wire operation.

Moreover, the connection part does not need to be divided, so that the number of parts can be made less than that of the adapter 50A, which relates to the second embodiment.

Also, the end part of the U-shaped part 33B can be engaged to a regulation member 60, so that the situation in which the U-shaped part 33B is unintentionally slid on circumference of the first cylindrical part 52a further than necessary, and the guidewire 40 contacts the operator operating the endoscope or the patient, causing annoyance, can be avoided.

Furthermore, since the first hooks 61 and the second hook 62 are respectively arranged, the guidewire 40 and the shaft 31 can be made parallel more easily by hooking the guidewire 40 or the shaft 31 on the respective hooks. Thus, when the guidewire 40 and the shaft 31 are gripped together and inserted or pulled out, both can be easily held and the operation of insertion and pulling out can be carried out more suitably.

Also, since the edge part of the endoscope locking part 54B is roundly chamfered, it can be attached without damaging the cylindrical part 13.

Also, since the flange parts 52c and 52d are provided, the U-shaped part 33B can easily be detached from the first catheter locking part 52B by twisting the U-shaped part 33B in contact with the flange parts 52c and 52d. In this case, the cutaway part 52e is arranged on the flange part 52c, so that it can be detached from the cutaway part 52e. Furthermore, the edge parts of the flange parts 52c and 52d including the cutaway part 52e and the U-shaped part 33B are roundly chamfered, so that the U-shaped part can be detached without them damaging each other.

Also, the distance between the attaching position C3 of the U-shaped part 33B of the treatment tool control part 32B and the guidewire lumen entry aperture 36 is from 30 mm to 45 mm, and since the first catheter locking part 52B is arranged on the connection part 51C to make the distance between the guidewire lumen entry aperture 36 and the forceps valve 14 to be 70 mm when the treatment tool control part 32B is locked on the first catheter locking part 52B, when moving the shaft 31 and the guidewire 40 back and forth together, a suitable distance for the operation can be secured between the guidewire lumen entry aperture 36 and the forceps valve 14, and a soft guidewire 40 can come out and go in through the guidewire lumen entry aperture 36 without being bent.

Figure 28:
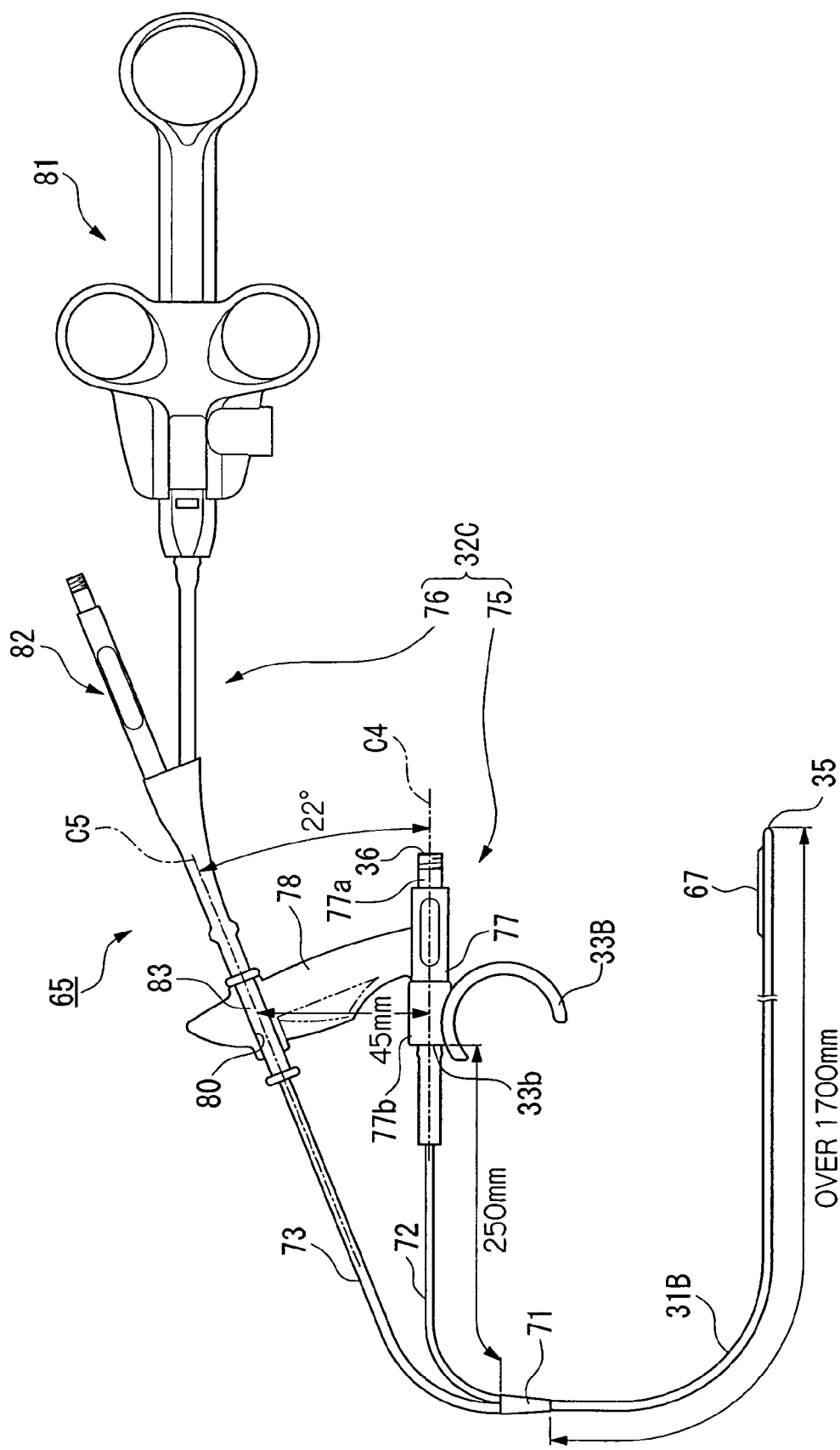
FIG. 28 is a plan view showing a papillotomy knife according to a fifth embodiment of the present invention.
Figure 29A:
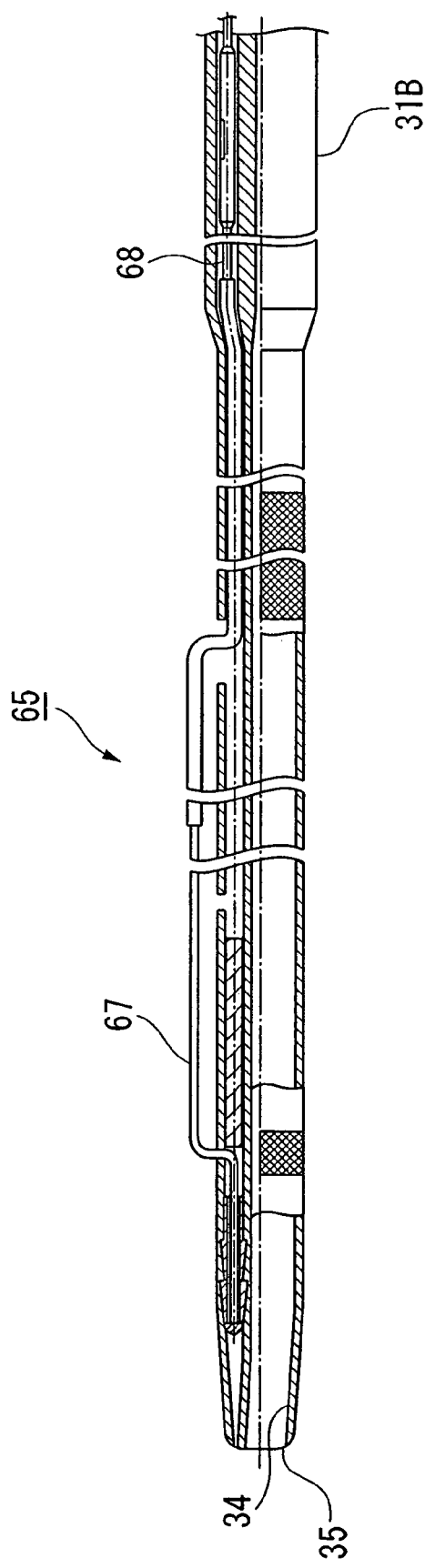
FIGS. 29A and 29B are cross-sectional view showing the relevant part of the papillotomy knife according to the fifth embodiment of the present invention.
Figure 29B:
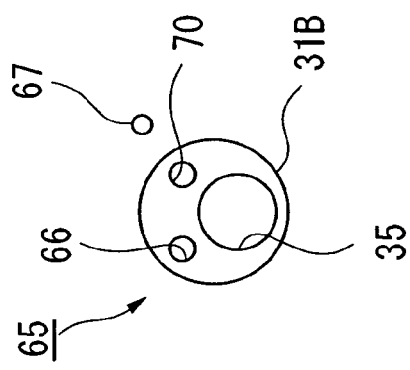
Figure 30:
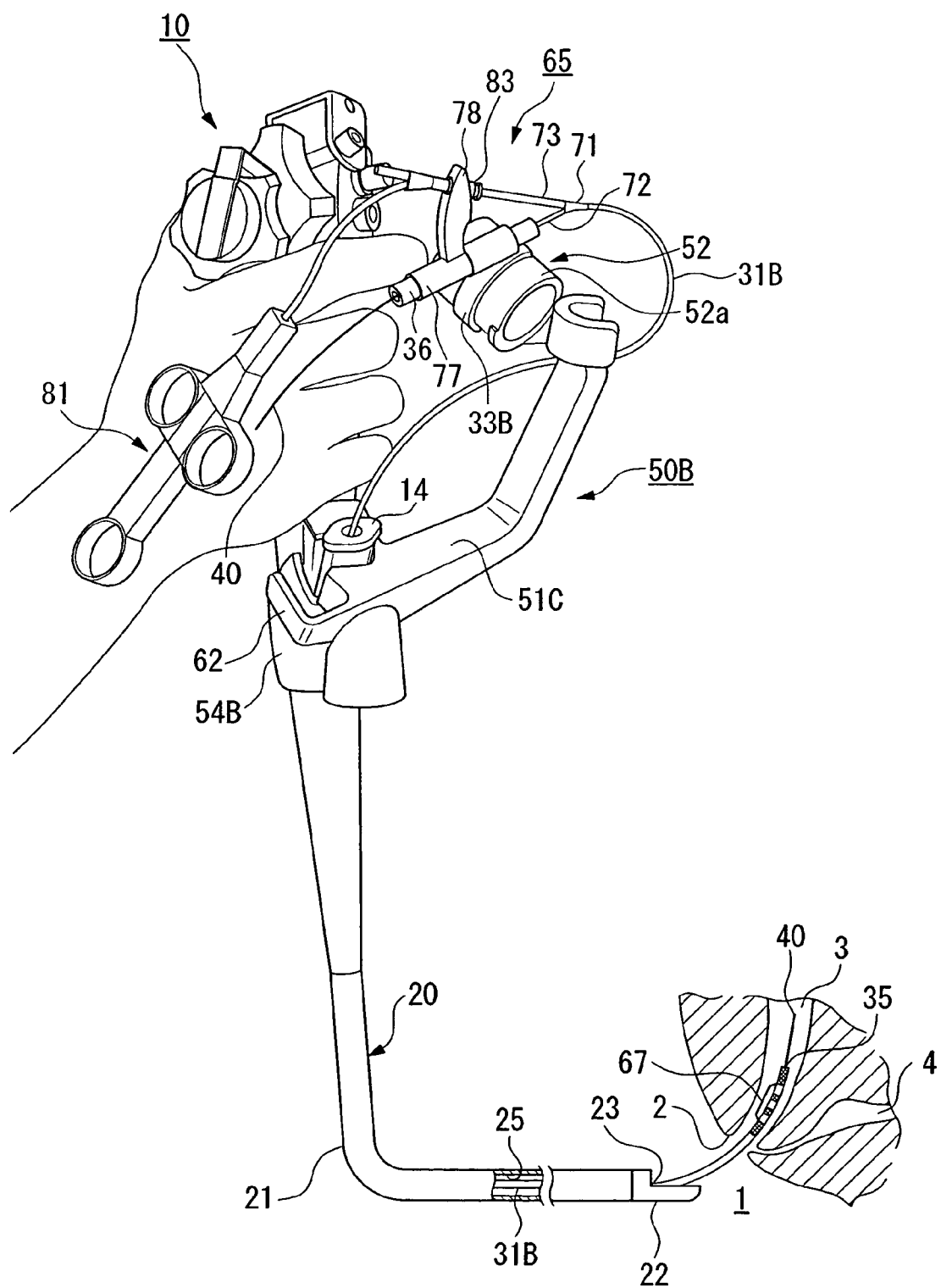
FIG. 30 is a diagram showing an aspect of the endoscope adapter being used in combination with an endoscope and a catheter, as a fifth embodiment of the endoscope adapter according to the present invention.

Next, as a fifth embodiment, a modification example of a treatment tool for the endoscope is described making reference to FIG. 28 to FIG. 30. Also, the same reference symbols are assigned to the same parts in the diagrams used for description so far, and their detailed descriptions are omitted.

The treatment tool used with the endoscope 10, which relates to the present embodiment, is a papillotomy knife 65 shown in FIG. 28.

The shaft 31B of the papillotomy knife 65 has; a fluid feeding lumen 66, which is separate from the guidewire lumen 34 through which the guidewire 40 can be passed, and is arranged along the guidewire lumen 34 and allows contrast medium and so forth to pass through; and a wire lumen 70, through which passes a wire part 68 that has a knife part 67, which carries out dissection of an affected duodenal papilla 2, connected to its end and that transfers hi-frequency electrical power to the knife part 67. The shaft 31 is bifurcated, at a bifurcation part 71, into a first tube sheath 72 that has the guidewire lumen 34 on its base end side, and a second tube sheath 73 having the fluid feeding lumen 66 and the wire lumen 70.

The treatment tool control part 32C has a first control part 75, which is connected to the base end of the first tube sheath 72 and controls the guidewire 40 to move back and forth, and a second control part 76, which is connected to the base end of the second tube sheath 73 and controls the knife part 67. Also, the second control part 76 can be freely attached and detached to and from the first control part 75.

The first control part 75 has a guidewire insertion part 77, which has the guidewire lumen entry aperture 36 on one end 77a allowing the guidewire 40 to pass through, and which is formed to be cylindrical to allow the guidewire 40 to pass through; and a control connection part 78 which connects the second control part 76 to the first control part 75 so that they are freely detachable. The first tube sheath 72 is connected to the other end 77b of the guidewire insertion part 77. The U-shaped part 33B is arranged on the guidewire insertion part 77.

The control connection part 78 is arranged standing on the side opposite from the U-shaped part 33B via the guidewire insertion part 77, and an engaging part 80 which can engage a locking part 83, described later, is arranged in the position at least 45 mm distant from the central axis of the guidewire insertion part 77 of the control connection part 78. This engaging part 80 is formed in a groove shape, and the central axis C5 is angled substantially 22 degrees from the central axis C4 of the guidewire insertion part 77.

The length of the first tube sheath 72 from the bifurcation part 71 to the attachment point of the U-shaped part 33B is made to be more than 250 mm. Also, the length of the shaft 31B from the guidewire lumen exit aperture 35 to the bifurcation part 71 is made to be 1700 mm.

The second control part 76 has a knife operation handle 81, which operates the wire part 68 to move back and forth in the wire lumen 70, a fluid feeding part 82 linked to the fluid feeding lumen 66, and the locking part 83, which can be attached to the first control part 75.

With this papillotomy knife 65, when changing treatment tools, the same kind of operation method employed in the fourth embodiment allows the same kind of effects and advantages, and the predetermined treatment can be carried out as shown in FIG. 30.

In this case, a single operator can carry out all operations relating to the papillotomy knife 65, but since the first tube sheath 72 and the second tube sheath 73 are branched, some operations can be passed on to an assistant by detaching the locking part 83 from the engaging part 80.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

For example, the U-shaped part 33B and the first catheter locking part 52B may respectively have the same color, and the first hooks 61 and the second hook 62 may be respectively marked with different colors. In this case, when operation instructions relating to each are given, these colors may be called so that clear instructions can be given.

The present invention is applicable for an application in which a guidewire is passed through inside a thin hollow body such as the shaft of a catheter, and an operation to relatively move the hollow body leaving the wire is required.

As explained above, an endoscope adapter of the present invention is a freely detachable adapter for an endoscope to be used with an endoscope that is provided with an endoscope control part, which an operator holds in hand and which carries out various operations, and an endoscope insertion part, one end of which is connected to the endoscope control part, and which is inserted into a body cavity from the other end side; and that is constructed so that as a shaft of a treatment tool provided with a guide wire lumen is inserted from a forceps plug provided in the endoscope control part into a forceps channel of the endoscope insertion part, the shaft is to be guided by a guidewire passing through the guide wire lumen, and inserted to a desired position inside the body cavity; the adapter including: a locking device for attaching and detaching that attaches and locks the adapter for an endoscope onto a predefined position on the endoscope control part; and a first treatment tool locking device that keeps the treatment tool at a first predefined position; and at the first predefined position, a guidewire entry aperture of the treatment tool and an entry aperture of the forceps plug are separated in such a way as to face each other along substantially the same line.

With this kind of endoscope adapter, the endoscope adapter is attached to a predetermined position on the endoscope control part by the locking device which attaches and detaches, and by locking the treatment tool to the first treatment tool locking device and holding it at the first predetermined position, the guidewire entry aperture of the treatment tool and the forceps plug entry aperture are separated opposing each other on substantially the same straight line, and thus a single operator can hold and move the guidewire and the shaft, which are next to each other and whose feeding directions are opposite to each other, the same amount in the same direction, that is, it becomes possible to pull out the abovementioned shaft and feed in the guidewire.

The adaptor for an endoscope may further include a second treatment tool locking device which holds the treatment tool at a second predetermined position wherein the guide wire entry aperture at the second predetermined position is made to be in substantially the same direction as the direction of operation of the guide wire in which the end part of the guide wire is moved to a required position in a body cavity. In this case, when normal operation in which the guide wire is inserted to the target position is carried out, the direction of movement of the guide wire operated by the operator and the direction of movement of the end part of the guide wire can be made to be substantially the same by locking the treatment tool to the second locking device and holding it at the second predetermined position.

The locking device for attaching and detaching may have a position determination device. In this case, the first predetermined position and the second predetermined position can be easily configured.

The first and second treatment tool locking devices may be respectively parts to be locked onto having a substantially circular cross section, and the treatment tool may be locked by engaging a substantially semi-cylindrical, U-shaped part, formed with elastic material and provided on the treatment tool control part, to the periphery of the part to be locked onto. In this case, it becomes possible to easily attach and remove the U-shaped part formed with elastic material on the treatment tool side to and from the part to be locked onto having a substantially circular cross section on the adapter side. In addition, the U-shaped part on the treatment tool side preferably has a handle that makes the removal easy using the principle of leverage.

The adaptor for an endoscope may further include a rod-shaped connection part, wherein the first and second treatment tool locking devices are respectively provided at both ends of the rod-shaped connection part. In this case, a single adapter for an endoscope has two predetermined positions.

The adaptor for an endoscope may further include: a first rod-shaped member, which has the part to be locked onto having a substantially circular cross section provided on its top end side; and a second rod-shaped member, which has the locking device for attaching and detaching provided on its bottom end side, are pivotably connected to the first rod-shaped member, wherein the part to be locked onto with the first and second rod-shaped members held in a straight line is taken to be the first predetermined position, and the part to be locked onto with the first and second rod-shaped members held in a bent shape is taken to be the second predetermined position, and the part to be locked onto is made to be selectively switchable between the first predetermined position and the second predetermined position. In this case, the single endoscope adapter has two predetermined positions.

The treatment tool may have a shaft extension part connected to the guidewire entry aperture, and the treatment tool locking device may be provided at the back end of the shaft extension part. In this case, an appropriate distance between the endoscope control part and the fluid feeding cap can be secured.

The endoscope of the present invention is provided with: an endoscope control part, which an operator holds in hand and which carries out various operations; an endoscope insertion part, one end of which is connected to the control part, and which is inserted into a body cavity from the other end side; a forceps plug provided in the endoscope control part; and a first treatment tool locking device that keeps a treatment tool at a first predefined position, wherein the endoscope is constructed so that as a shaft of the treatment tool provided with a guide wire lumen is inserted from the forceps plug into a forceps channel of the endoscope insertion part, the shaft is to be guided by a guidewire passing through the guide wire lumen, and inserted to a desired position inside the body cavity, and wherein at the first predefined position, a guidewire entry aperture of the treatment tool and an entry aperture of the forceps plug are separated in such a way as to face each other along substantially the same line.

With this kind of endoscope, by locking the treatment tool to the first treatment tool locking device and holding it at the first predetermined position, the guidewire entry aperture of the treatment tool and the forceps plug entry aperture become separated opposing each other on substantially the same straight line, and thus a single operator can hold and move the guidewire and the shaft, which are next to each other and whose feeding directions are opposite to each other, the same amount in the same direction, that is, it becomes possible to pull out the abovementioned shaft and feed in the guidewire.

The endoscope may further include a second treatment tool locking device which holds the treatment tool at a second predetermined position is provided, wherein the guide wire entry aperture at the second predetermined position is made to be in substantially the same direction as the direction of operation of the guide wire in which the end part of the guide wire is moved to a required position in a body cavity. In this case, when normal operation, in which the guide wire is inserted to the target position, is carried out, the direction of movement of the guide wire operated by the operator and the direction of movement of the end part of the guide wire can be made to be substantially the same by locking the treatment tool to the second locking device and holding it at the second predetermined position.

The first and second treatment tool locking devices may be respectively parts to be locked onto having a substantially circular cross section, and the treatment tool may be locked by engaging a substantially semi-cylindrical U-shaped part, formed with elastic material and provided on a treatment tool control part to the periphery of the part to be locked onto. In this case, it becomes possible to easily attach and detach the U-shaped part, formed with elastic material on the treatment tool side, to and from the part to be locked onto having a substantially circular cross section on the adapter side. In this case, the U-shaped part on the treatment tool side preferably has a handle that makes the removal easy using the principle of leverage.

The endoscope may further include a first rod-shaped member, which has a part to be locked onto having a substantially circular cross section, provided on its top end side, and a second rod-shaped member, which is locked on the endoscope control part, are pivotably connected each other, wherein the part to be locked onto with the first and second rod-shaped members held in a straight line is taken to be the first predetermined position, and the part to be locked onto with the first and second rod-shaped members held in a bent shape is taken to be the second predetermined position, and they are made selectively switchable. In this case, it becomes possible to use a single part to be locked onto as two predetermined positions.

The treatment tool may have a shaft extension part connected to the guidewire entry aperture, and the treatment tool locking device may be provided at the back end of the shaft extension part. In this case, an appropriate distance between the endoscope control part and the fluid feeding cap can be secured.

With the endoscope adapter of the present invention, by attaching the endoscope adapter to the predetermined position on the endoscope control part by means of the locking device for attaching and detaching and using it, the guidewire entry aperture of the treatment tool and the forceps valve entry aperture are separated opposing each other on substantially the same straight line, and since it becomes possible for a single operator to control the guidewire and the shaft, which are next to each other and whose feeding directions are opposite to each other, with one hand and to move them the same amount in the same direction, the guidewire becomes relatively locked and the operation of changing treatment tools such as a catheter can be quickly carried out by a single person. Thus, endoscopic treatment time can be shortened, and the strain on the operator who controls the endoscope, the assistant and the patient can be reduced.

Also, the training time required for the operator and the assistant to gain proficiency in cooperative operation can be eliminated.

Furthermore, with the endoscope of the present invention, the guidewire entry aperture of the treatment tool and the forceps valve entry aperture are separated opposing each other on substantially the same straight line, and since it becomes possible for a single operator to control the guidewire and the shaft, which are next to each other and whose feeding directions are opposite to each other, with one hand and to move them the same amount in the same direction, the guidewire becomes relatively locked and the operation of changing treatment tools such as a catheter can be quickly carried out by a single person. Thus, endoscopic treatment time can be shortened, and the strain on the operator who controls the endoscope, the assistant and the patient can be reduced.

Also, the training time required for the operator and the assistant to gain proficiency in cooperative operation can be eliminated.

What is claimed is:

1. A freely detachable adapter for an endoscope to be used with an endoscope that is provided with an endoscope control part, which an operator holds in hand and which carries out various operations, and an endoscope insertion part, one end of which is connected to the endoscope control part, and which is inserted into a body cavity from the other end side; and that is constructed so that a shaft of a treatment tool provided with a guide wire lumen is inserted from a forceps plug provided in the endoscope control part into a forceps channel of the endoscope insertion part, the shaft is to be guided by a guidewire passing through the guide wire lumen, and inserted to a desired position inside the body cavity; the adapter comprising: a locking device for attaching and detaching that attaches and locks the adapter for an endoscope onto a predefined position on the endoscope control part; and a first treatment tool locking device that keeps the treatment tool at a first predefined position wherein, at the first predefined position, a guidewire entry aperture of the treatment tool and an entry aperture of the forceps plug are separated in such a way as to face each other, and the guidewire extending from an inside of the guidewire entry aperture and the shaft extending from an inside of the entry aperture of the forceps plug are extended in an opposite direction, and are adjacent to each other.

2. The adapter for an endoscope according to claim 1, further comprising
    a second treatment tool locking device which holds the treatment tool at a second predetermined position wherein the guide wire entry aperture at the second predetermined position is made to be in substantially the same direction as the direction of operation of the guide wire in which the end part of the guide wire is moved to a required position in a body cavity.

3. The adapter for an endoscope according to claim 1, wherein the locking device for attaching and detaching has a position determination device.

4. The adapter for an endoscope according to claim 1, wherein
    the first treatment tool locking device and a second treatment tool locking device are respectively parts to be locked onto having a substantially circular cross section, and the treatment tool is locked by engaging a substantially semi-cylindrical, U-shaped part, formed with elastic material and provided on the treatment tool control part, to the periphery of the part to be locked onto.

5. The adapter for an endoscope according to claim 4, further comprising a rod-shaped connection part, wherein the first and second treatment tool locking devices are respectively provided at both ends of the rod-shaped connection part.

6. The adapter for an endoscope according to claim 2, further comprising:
   a first rod-shaped member, which has the part to be locked onto having a substantially circular cross section provided on its top end side; and a second rod-shaped member, which has the locking device for attaching and detaching provided on its bottom end side, are pivotably connected to the first rod-shaped member, wherein
   the part to be locked onto with the first and second rod-shaped members held in a straight line is taken to be the first predetermined position, and the part to be locked onto with the first and second rod-shaped members held in a bent shape is taken to be the second predetermined position, and the part to be locked onto is made to be selectively switchable between the first predetermined position and the second predetermined position.

7. The adapter for an endoscope according to claim 1, wherein
   the treatment tool has a shaft extension part connected to the guidewire entry aperture, and the treatment tool locking device is provided at the back end of the shaft extension part.

8. An endoscope provided with: an endoscope control part, which an operator holds in hand and which carries out various operations; an endoscope insertion part, one end of which is connected to the control part, and which is inserted into a body cavity from the other end side; a forceps plug provided in the endoscope control part; and a first treatment tool locking device that keeps a treatment tool at a first predefined position, wherein the endoscope is constructed so that a shaft of the treatment tool provided with a guide wire lumen is inserted from the forceps plug into a forceps channel of the endoscope insertion part, the shaft is to be guided by a guidewire passing through the guide wire lumen, and inserted to a desired position inside the body cavity, and wherein at the first predefined position, a guidewire entry aperture of the treatment tool and an entry aperture of the forceps plug are separated in such a way as to face each other, and the guidewire extending from an inside of the guidewire entry aperture and the shaft extending from an inside of the entry aperture of the forceps plug are extended in an opposite direction, and are adjacent to each other.

9. The endoscope according to claim 8, further comprising a second treatment tool locking device which holds the treatment tool at a second predetermined position is provided, wherein
   the guide wire entry aperture at the second predetermined position is made to be in substantially the same direction as the direction of operation of the guide wire in which the end part of the guide wire is moved to a required position in a body cavity.

10. The endoscope according to claim 8, wherein
    the first treatment tool locking device and a second treatment tool locking device are respectively parts to be locked onto having a substantially circular cross section, and the treatment tool is locked by engaging a substantially semi-cylindrical U-shaped part, formed with elastic material and provided on a treatment tool control part to the periphery of the part to be locked onto.

11. The endoscope according to claim 8, further comprising a first rod-shaped member, which has a part to be locked onto having a substantially circular cross section, provided on its top end side, and a second rod-shaped member, which is locked on the endoscope control part, are pivotably connected each other, wherein
    the part to be locked onto with the first and second rod-shaped members held in a straight line is taken to be the first predetermined position, and the part to be locked onto with the first and second rod-shaped members held in a bent shape is taken to be the second predetermined position, and they are made selectively switchable.

12. The endoscope according to claim 8, wherein
    the treatment tool has a shaft extension part connected to the guidewire entry aperture, and the treatment tool locking device is provided at the back end of the shaft extension part.

* * * * *